US011191815B2

(12) United States Patent
Gu et al.

(10) Patent No.: US 11,191,815 B2
(45) Date of Patent: Dec. 7, 2021

(54) GLUCOSE-RESPONSIVE INSULIN DELIVERY MICRONEEDLE SYSTEM

(71) Applicant: North Carolina State University, Raleigh, NC (US)

(72) Inventors: Zhen Gu, Apex, NC (US); Jicheng Yu, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/567,532

(22) PCT Filed: Apr. 21, 2016

(86) PCT No.: PCT/US2016/028605
§ 371 (c)(1),
(2) Date: Oct. 18, 2017

(87) PCT Pub. No.: WO2016/017320
PCT Pub. Date: Oct. 27, 2016

(65) Prior Publication Data
US 2018/0110841 A1   Apr. 26, 2018

Related U.S. Application Data

(60) Provisional application No. 62/150,622, filed on Apr. 21, 2015.

(51) Int. Cl.
| | |
|---|---|
| *A61K 38/44* | (2006.01) |
| *A61K 9/00* | (2006.01) |
| *A61K 9/70* | (2006.01) |
| *A61P 3/10* | (2006.01) |
| *A61K 38/28* | (2006.01) |
| *A61K 9/51* | (2006.01) |
| *A61M 37/00* | (2006.01) |
| *A61K 9/107* | (2006.01) |

(52) U.S. Cl.
CPC ............ *A61K 38/44* (2013.01); *A61K 9/0021* (2013.01); *A61K 9/0024* (2013.01); *A61K 9/1075* (2013.01); *A61K 9/5161* (2013.01); *A61K 9/5192* (2013.01); *A61K 9/7023* (2013.01); *A61K 38/28* (2013.01); *A61M 37/0015* (2013.01); *A61P 3/10* (2018.01); *C12Y 101/03004* (2013.01); *A61M 2037/0023* (2013.01); *A61M 2037/0046* (2013.01); *A61M 2207/00* (2013.01)

(58) Field of Classification Search
CPC .... A61K 38/44; A61K 9/0024; A61K 9/7023; A61K 9/0021; A61P 3/10; C12Y 101/03004; A61M 37/0015
See application file for complete search history.

(56) References Cited

U.S. PATENT DOCUMENTS

| | | | |
|---|---|---|---|
| 6,960,617 B2 | 11/2005 | Omidian et al. | |
| 2002/0197261 A1* | 12/2002 | Li .................. | A61K 51/088 |
| | | | 424/178.1 |
| 2004/0265386 A1 | 12/2004 | Taylor | |
| 2008/0102114 A1 | 5/2008 | Koritala et al. | |
| 2010/0276319 A1 | 11/2010 | Clarke | |
| 2011/0177139 A1 | 7/2011 | Jung et al. | |
| 2012/0046651 A1 | 2/2012 | Beyer et al. | |
| 2015/0030641 A1 | 1/2015 | Anderson et al. | |
| 2018/0333495 A1 | 11/2018 | Matsumoto et al. | |

FOREIGN PATENT DOCUMENTS

| | | |
|---|---|---|
| CN | 104353062 A | 2/2015 |
| CN | 107530296 B | 6/2021 |
| EP | 3285750 | 9/2020 |
| HK | 1245105 | 4/2021 |
| IN | 378574 | 4/2021 |
| JP | 2005-083928 | 3/2005 |
| NG | PT/C/2017/2447 | 3/2018 |
| RU | 2719584 | 4/2020 |
| WO | WO 2007/012114 A1 | 2/2007 |
| WO | WO 2007/075388 A2 | 7/2007 |

(Continued)

OTHER PUBLICATIONS

Bariya et al. Microneedles: An Emerging Transdermal Drug Delivery System; Journal of Pharmacy and Pharmacology, vol. 64, pp. 11-29. (Year: 2011).*
Gu et al. Glucose-Responsive Microgels Integrated With Enzyme Nanocapsules for Closed-Loop Insulin Delivery; ACS-Nano, vol. 7, No. 8, pp. 6758-6766. (Year: 2013).*
Takiyama et al. Hypoxia in Diabetic Kidneys; Biomed Research International, vol. 2014, pp. 1-10. (Year: 2014).*
Lee et al. Nanoparticle Popsicle: Transdermal Delivery of Nanoparticles Using Polymeric Microneedle Array; Korean Journal of Chemical Engineering, vol. 28, No. 9, pp. 1913-1917. (Year: 2011).*
Aronoff et al. (1975) Complexation of D-glucose with borate. Carbohydr. Res. 40(2):299-309.
Communication of European publication number and information on the application of Article 67(3) EPC corresponding to European Patent Application No. EP16783841.6 dated Jan. 31, 2018.

(Continued)

*Primary Examiner* — Susan M Hanley
*Assistant Examiner* — Paul C Martin
(74) *Attorney, Agent, or Firm* — Jenkins, Wilson, Taylor & Hunt, P.A.

(57) ABSTRACT

A closed-loop insulin delivery system is described. More particularly, the presently disclosed insulin delivery system can comprise glucose-responsive vesicles that release insulin in response to hypoxia triggered by enzymatic reduction of glucose. In addition or as an alternative to insulin, the delivery system can release other diabetes treatment agents, such as non-insulin-based diabetes treatment agents. The vesicles can be prepared from a hypoxia sensitive polymer, such as a hypoxia-sensitive hyaluronic acid (HS-HA). The HS-HA can comprise hydrophobic groups that can be reduced in hypoxic environments to form hydrophilic groups. The vesicles can be loaded into microneedles and microneedle array patches for use in the treatment of diabetes or to otherwise regulate blood glucose levels in subjects in need of such treatment.

23 Claims, 5 Drawing Sheets

(56) References Cited

FOREIGN PATENT DOCUMENTS

| WO | WO 2010/040271 A1 | 4/2010 |
|---|---|---|
| WO | WO 2010/088300 A1 | 8/2010 |
| WO | WO 2012/050179 | 4/2012 |
| WO | WO 2013/123492 A2 | 8/2013 |
| WO | WO 2014/179344 A1 | 11/2014 |
| WO | WO 2017/143153 A1 | 6/2017 |
| WO | WO 2018/085809 A1 | 5/2018 |

OTHER PUBLICATIONS

Edwards (1993) Nitroimidazole drugs—action and resistance mechanisms. I. Mechanisms of action. J. Antimicrob. Chemother. 31(1):9-20.

Fercher et al. (2011) Intracellular O2 Sensing Probe Based on Cell-Penetrating Phosphorescent Nanoparticles. Acs Nano 5(7):5499-5508.

Gordijo et al. (2011) Nanotechnology-Enabled Closed Loop Insulin Delivery Device: In Vitro and In Vivo Evaluation of Glucose-Regulated Insulin Release for Diabetes Control. Adv. Funct. Mater. 21(1):73-82.

Gu et al. (2013) Injectable Nano-Network for Glucose-Mediated Insulin Delivery. ACS Nano 7(5):4194-4201.

Kataoka et al. (1998) Totally Synthetic Polymer Gels Responding to External Glucose Concentration: Their Preparation and Application to On-Off Regulation of Insulin Release. J. Am. Chem. Soc. 120(48):12694-12695.

Kim et al. (1990) Self-regulated glycosylated insulin delivery. J. Controlled Release 11(1):193-201.

Michaels et al. (1975) Drug permeation through human skin. Theory and in vitro experimental measurements. AIChE J 21(5):985-996.

Mo et al. (2014) Emerging micro- and nanotechnology based synthetic apporaches for insulin delivery. Chemical Society Reviews 43(10):3595-3629.

Narayan (2014) Transdermal Delivery of Insulin via Microneedles. J. Biomedical Nanotechnology 10:2244-2260.

Notice of Acceptance corresponding to Nigerian Patent Application No. NGPCT20172447 dated Dec. 19, 2017.

Nunn et al. (1995) Nitroimidazoles and imaging hypoxia. Eur. J. Nucl. Med. 22(3):265-280.

Office Action corresponding to Colombian Patent Application No. NC2017/0011422 dated Nov. 17, 2017.

Owens et al. (2007) Insulins today and beyond. Lancet 358(9283):739-746.

Pickup et al. (2008) Nanomedicine and its potential in diabetes research and practice. Diabetes—Metabolism Research and Reviews 24(8):604-610.

Ravaine et al. (2008) Chemically controlled closed-loop insulin delivery. Journal of Controlled Release 132:2-11.

Stumvoll et al. (2005) Type 2 diabetes: principles of pathogenesis and therapy. Lancet 365(9467):1333-1346.

Thambi et al. (2013) Hyoxia-responsive polymeric nanoparticles for tumor-targeted drug delivery. Biomaterials 35(5):1735-1743.

Will et al. (2006) Analysis of mitochondrial function using phosphorescent oxygen-sensitive probes. Nat. Protoc. 1:2563-2572.

Wu et al. (2011) Organization of Glucose-Responsive Systems and Their Properties. Chem. Rev. 111(12):7855-7875.

Chu et al. (2012), "In vitro and in vivo testing of glucose-responsive insuin-delivery microdevices in diabetic rats," The Royal Society of Chemistry, vol. 12, No. 14, pp. 2533-2539.

Extended European Search Report corresponding to European Patent Application Serial No. 16783841.6 dated Nov. 12, 2018.

IPRP corresponding to International Patent Application Serial No. PCT/US2016/028605 dated Oct. 24, 2017.

Office Action corresponding to Panama Patent Application Serial No. 9181601 dated Jul. 17, 2018.

Office Action corresponding to Israeli Patent Application Serial No. 255155 dated Aug. 15, 2018.

Office Action (Notice of Opposition) corresponding to Ecuador Patent Application Serial No. 2017-73558 dated Dec. 3, 2018.

Office Action corresponding to Columbian Patent Application Serial No. NC2017/0011422 dated Jan. 14, 2019.

Bratlie et al. (2012) Materials for diabetecs therapeutics. Advanced Healthcare Materials 1(3):1-33.

Dowd et al. (1983) Measurement of transcutaneous oxygen pressure in health and peripheral arterial occlusive disease. Journal of Bone and Joint Surgery, British vol. 65-B(1):79-83.

Fletcher (1980) On Facilitated Oxygen Diffusion in Muscle Tissues. Biophys. J. 29(3):437-458.

Krohn et al. (2008) Molecular imaging of hypoxia. J. Nucl. Med. 49(Suppl. 2): 129S-148S.

Ling & Chen (2013) Dissolving polmer microneedle patches for rapid and efficent transdermal delivery of insulin to diabetic rats. Acta Biomaterialia 9:8952-8961.

Martanto et al. (2004) Transdermal delivery of insulin using microneedles in vivo. Pharmaceutical Research 21(6):947-952.

Notification Concerning Availability of the Publication of the International Application corresponding to International application No. PCT/US2016/028605 dated Oct. 27, 2016.

Notification of Transmittal of the International Search Report and the Written Opinion of the International Searching Authority, or the Declaration corresponding to International application No. PCT/US2016/028605 dated Jul. 15, 2017.

Prausnitz & Langer (2008) Transdermal drug delivery. Nature Biotechnology 26(11):1-18.

Tabák et al. (2012) Prediabetes: a high-risk state for diabetes development. Lancet 379(9833):1-23.

Takasawa et al. (2008) Applications of Nitroimidazole In Vivo Hypoxia Imaging in Ischemic Stroke. Stroke 339(5):1629-1637.

Tiegs et al. (1992) A T cell-dependent experimental liver injury in mice inducible by concanavalin A. J. Clin. Invest. 90(1):196.

Veiseh et al. (2015) Managing diabetes with nanomedicine: challenges and opportunities. Nature Reviews Drug Discovery 14(1):1-30.

Yang et al. (2013) A bio-inspired swellable microneedle adhesive for mechanical interlocking with tissue. Nature Communications 4:1-10.

Yu et al. (2015) Microneedle-array patches loaded with hypoxia-sensitive vesicles provide fast glucose-responsive insulin delivery. PNAS 112(27):8260-8265.

Office Action corresponding to Israeli Patent Application No. 255155 dated May 5, 2019.

Beers et al. (1952). "A Spectrophotometric Method for Measuring the Breakdown of Hydrogen Peroxide by Catalase," J. Biol. Chem. 195(1):133-140.

Chen et al., "Glucose-Responsive Microneedle Patches for Diabetes Treatment," Journal of Diabetes Science and Technology, vol. 13(1), pp. 41-48 (2019).

Chou et al. (2015), "Glucose-responsive insulin activity by covalent modification with aliphatic phenylboronic acid conjugates," Proc. Natl. Acad. Sci. USA, 112(8):2401-2406.

Fischel-Ghodsian et al. (1988), "Enzymatically controlled drug delivery," Proc. Natl. Acad. Sci. USA, 85(7):2403-2406.

Gilroy et al. (2016) "Controlled Release of Biologics for the Treatment of Type 2 Diabetes," Author Manuscript, published in final edited form in J. Controlled Release, vol. 240, pp. 151-165 http.//dx.doi.org/10.1016/j.jconrel.2015/12/002 (14 pages).

Grant Decision corresponding to Kazakhstan Patent Application No. 20171060.1 dated May 13, 2019.

Heo et al. (2011) "Long-term In Vivo Glucose Monitoring using Fluorescent Hydrogel Fibers," Proc. Natl. Acad. Sci USA 108(33):13399-13403.

Liu et al. (2013) "Biomimetic enzyme nanocomplexes and their use as antidotes and preventive measures for alcohol intoxication," Nat. Nanotechnol. 8(3):187-192.

MIT Technology Review, "35 Innovators Under 35," https://www.technologyreview.com/lists/innovators-under-35/2015/, pp. 1-11 (2015) [retrieved online Nov. 11, 2019].

Notification of Transmittal of the International Search Report and the Written Opinion of the International Searching Authority, or the

(56) References Cited

OTHER PUBLICATIONS

Declaration corresponding to International application No. PCT/US2017/060352 dated Jan. 11, 2018.
Notification of Transmittal of International Preliminary Report on Patentability (Chapter 1 of the Patent Cooperation Treaty) corresponding to International application No. PCT/US2017/060325 dated May 16, 2019.
Office Action (Technical Examination) corresponding to Columbian Patent Application No. NC2017/0011422 dated Jun. 18, 2019.
Podual et al. (2000) "Preparation and dynamic response of cationic copolymer hydrogels containing glucose oxidase," Polymer 41(11):3975-3983.
Prausnitz (2004) "Mirconeedles for transdermal drug delivery," Adv. Drug Deliv., Rev. 56(5):581-587.
Rogers, "Top 10 images of 2015," ScienceMag.org, https://www.sciencemag.org/news/2015/12/top-10-images-2015 dated Dec. 23, 2015, pp. 1-16 [retrieved online Nov. 11, 2019].
Saravanakumar et al., "Reactive-oxygen-species-responsive drug delivery systems: promises and challenges," Advanced Science, 44:1600124 (Jun. 8, 2016) (pp. 1-19).
Tai et al. (2014) "Bio-inspired synthetic nanovesicles for glucose-responsive release of insulin," Biomacromolecules 15(10):3495-3502.
Veiseh et al. (2015) "A smart insulin patch," Nature, vol. 524, pp. 39-40.
Wang et al., "Glucose-Responsive Insulin and Delivery Systems: Innovation and Translation," Advanced Materials, 1902004, pp. 1-19 (2019).
Yu et al., "Stimuli-responsive delivery of therapeutics for diabetes treatment," Bioengineering & Translational Medicine, 1:323-337 (Oct. 3, 2016).
Zhang et al., "Design and fabrication of MEMS-based microneedle arrays for medical applications," Microsystem Technologies, vol. 15, Iss. 7, pp. 1073-1082 (2009).
Office Action corresponding to Russian Patent Application No. 2017139931 dated Dec. 13, 2019.
Office Action corresponding to Chilean Patent Application No. 2017-002652 dated Jan. 20, 2020.
Office Action corresponding to Indian Patent Application No. 201727037788 dated Feb. 11, 2020.
Office Action (Notice of Reeason for Rejection) corresponding to Japanese Patent Application No. 2017-555709 dated Mar. 9, 2020.
Decision to Grant corresponding to Russian Patent Application No. 2017139931 dated Feb. 6, 2020.
Examination Report corresponding to Australian application No. 2016252738 dated Jul. 9, 2020.
Intent to Grant corresponding to European Application No. 16783841.6 dated May 25, 2020.
Office Action corresponding to Mexican Patent Application Serial No. 2017/013337 dated Jul. 14, 2020.
Decision to Grant corresponding to European Patent Application No. EP16783841.6 dated Sep. 24, 2020.
Office Action (Notice of Reason for Rejection) corresponding to Japanese Patent Application No. 2017-555709 dated Oct. 26, 2020.
Pickup (2012) "Insulin-pump therapy for type 1 diabetes mellitus," New Engl. J. Med., 366(17): 1616-1624.
Tang et al., "Water-Soluble Poly(L-serine)s with Elongated and Charged Side-Chains: Synthesis, Conformations and Cell-Penetrating Properties," Biomacromolecules, vol. 13, pp. 2609-2615 (2012).
Bonnet et al. "Novel nitroimidazole alkylsulfonamides as hypoxic cell radiosensitisers," Bioorg. Med. Chem. vol. 22, pp. 2123-2132 (2014).
Huo et al. "Redox-responsive polymers for drug delivery: from molecular design to applications," Polym. Chem. vol. 5, pp. 1519-1528 (2014).
Kang et al. "A sulfonamide based glucose-responsive hydrogel with covalently immobilized glucose oxidase and catalase," J. Controlled Release vol. 86, pp. 115-121 (2003).
Kohen, R., "Skin antioxidants: their role in aging and in oxidative stress-new approaches for their evaluation," Biomed. Pharmacother. vol. 53, pp. 181-192 (1999).
Liu et al., "Preparation and characterization of novel hyaluronic acid microneedles for insulin transdermal delivery," Journal of Shenyang Pharmaceutical University, vol. 27, No. 1, pp. 6-11 (2010). abstract only.
Makino et al., "A Microcapsule self-regulating delivery system for insulin," J. Controlled Release, vol. 12 pp. 235-239 (1990).
Matsumoto et al. "High Index Resist for 193 nm Immersion Lithography," Macromolecules vol. 41, pp. 5674-5680 (2008).
Napoli et al. "Oxidation-responsive polymeric vesicles," Nat. Mater. Vol. 3, pp. 183-189 (2004).
Napoli et al., "New Synthetic Methodologies for Amphiphilic Multiblock Copolymers of Ethylene Glycol and Propylene Sulfide," Macromolecules, vol. 34, pp. 8913-8917 (2001).
Office Action corresponding to Ukranian Patent Application No. 2017-10540 dated Nov. 16, 2020.
Office Action corresponding to Chinese Patent Application No. 2016800233776 dated Nov. 9, 2020.
Office Action corresponding to Australian Patent Application No. 2016252738 dated Nov. 24, 2020.
Ohkubo et al., "Intensive insulin therapy prevents the progression of diabetic microvascular complications in Japanese patients with non-insulin-dependent diabetes mellitus: a randomized prospective 6-year study," Diabetes Res. Clin. Pract., vol. 28, pp. 103-117 (1995).
Podual et al., "Glucose-sensitivity of glucose oxidase-containing cationic copolymer hydrogels having poly(ethylene glycol) grafts," J. Controlled Release, vol. 67, pp. 9-17 (2000).
Seki et al., "Accumulation of 2-aminoimidazole by *Streptomyces eurocidicus*," J Biochem, vol. 67, pp. 389-396 (1970).
Traitel et al., "Characterization of glucose-sensitive insulin release systems in simulated in vivo conditions," Biomaterials vol. 21, pp. 1679-1687 (2000).
Zhang et al., "Modulated insulin permeation across a glucose-sensitive polymeric composite membrane," J. Controlled Release vol. 80, pp. 169-178 (2002).
Decision to Grant corresponding to Japanese Patent Application No. 2017-555709 dated Feb. 22, 2021.
European Search Report corresponding to European Patent Application Serial No. 20202740 dated Feb. 19, 2021.
Notice of Publication corresponding to European Patent Application Serial No. 20202740 dated Feb. 21, 2021.
Notice of Grant corresponding to Mexican Patent Application Serial No. 2017013337 dated Feb. 11, 2021.
Hearing Notice corresponding to Indian Patent Application No. 2017237037788 dated Feb. 26, 2021.
Office Action corresponding to Vietnamese Patent Application Serial No. 1-2017-04619 dated Feb. 24, 2021.
Miki, H. "Fully synthetic artificial pancreas using smart gel," CMC Publishing Company, 2014, pp. 233-240 (Written in Japanese but submitted with copy of an English translation of an office action in a counterpart Japanese patent application corresponding to the subject U.S. patent application. The relevance of Miki is described in the office action where Miki is Reference 5.).
Office Action corresponding to Philippines Patent Application Serial No. 12017501910 dated Dec. 1, 2020.
Miki, H. "Fully synthetic artificial pancreas using smart gel," CMC Publishing Company, 2014, pp. 233-240 (English Translation and Written in Japanese).
Examination Report corresponding to Indonesian Patent Application No. PID201708190 dated Jun. 14, 2021.
Notice of Acceptance corresponding to Australian Patent Application No. 2016252738 dated Jun. 21, 2021.
Office Action corresponding to U.S. Appl. No. 16/347,536 dated Sep. 10, 2021.

\* cited by examiner

GLUCOSE-RESPONSIVE INSULIN DELIVERY MICRONEEDLE SYSTEM

RELATED APPLICATIONS

This application is a national stage application of PCT/US2016/028605, filed on Apr. 21, 2016, which claims priority to and the benefit of U.S. Provisional Patent Application No. 62/150,622, filed Apr. 21, 2015, the disclosure of which is incorporated herein by reference in its entirety.

TECHNICAL FIELD

The presently disclosed subject matter relates to systems and compositions, such as vesicles, nanoparticles, microneedles, and microneedle arrays, for the glucose-sensitive delivery of diabetes treatment agents, such as insulin and/or bioactive derivatives thereof. The presently disclosed subject matter further relates to methods of preparing the compositions and to methods of delivering diabetes treatment agents to a subject in need thereof.

ABBREVIATIONS

° C.=degrees Celsius
%=percentage
μL=microliter
μm=micrometer or micron
μs=microseconds
a.u.=absorbance units
BOC=tert-butyloxycarbonyl
CD=circular dichroism
DI=deionized
dL=deciliter
DLS=dynamic light scattering
DMF=dimethylformamide
EDC=N-(3-dimethylaminopropyl)-N'-ethylcarbodiimide hydrochloride
ELISA=enzyme linked immunosorbent
FESEM=field-emission scanning electron microscope
FITC=fluorescein isothiocyante
GOx=glucose oxidase
GRV=glucose-responsive vesicle
h=hour
HA=hyaluronic acid
HS=hypoxia-sensitive
IU=international units
KCl=potassium chloride
$K_2CO_3$=potassium carbonate
kDa=kiloDalton
kg=kilogram
$KH_2PO_4$=monopotassium phosphate
LC=loading capacity
MBA=N,N'-methylene bisacrylamide
mg=milligram
m-HA=acrylate-modified hyaluoric acid
min=minutes
mL=milliliter
mm=millimeter
mM=millimolar
MN=microneedle
mV=millivolt
N=Newton
NaCl=sodium chloride
NADPH=nicotinamide adenine dinucleotide phosphate
$Na_2HPO_4$=disodium phosphate
NHS=N-hydroxysuccinimide
NI=2-nitroimidazole
nm=nanometer
NMR=nuclear magnetic resonance
$O_2$=oxygen
PBS=phosphate buffered saline
pI=isoelectric point
RT=room temperature
SEM=scanning electron microscope
STZ=streptozotocin
TEM=transmission electron microscope
UV=ultraviolet
Zn=zinc

BACKGROUND

Diabetes mellitus is a group of metabolic diseases characterized by accumulation of glucose in the blood. See Pickup et al., Diabetes-Metabolism Research and Reviews, 24, 604-610 (2008); and Stumvoll et al., Lancet, 365, 1333-1346 (2005). As of 2014, 387 million people suffer from diabetes worldwide, and the number is estimated to be 592 million by 2035. See Mo et al., Chemical Society Reviews, 43, 3595-3629 (2014); and Tabák et al., Lancet, 379, 2279-2290 (2012). The traditional care for diabetics involves continuous monitoring of blood glucose levels and subsequent insulin injections to maintain normoglycemia. See Owens et al., Lancet, 358, 739-746 (2001). However, such self-administration can be associated with pain and limited glucose control. See Bratlie et al., Advanced Healthcare Materials, 1, 267-284 (2012); and Ravaine et al., Journal of Controlled Release, 132, 2-11 (2008).

Over the past decade, the development of transdermal injection devices with micron-scale needles for insulin delivery has been attempted. See Martanto et al., Pharmaceutical Research 21, 947-952 (2004); Narayan, J. Biomedical Nanotechnology, 10, 2244-2260 (2014); Ling et al., Acta Biomaterialia, 9, 8952-8961 (2013); Prausnitz et al., Nature Biotechnology, 26, 1261-1268 (2008); and Yang et al., Nature Communications, 4, (2013), doi 10.1038/ncomms2715. Yet, there is still a need for additional insulin delivery systems and related compositions, particularly for "closed-loop" delivery systems that can deliver insulin to a subject rapidly in response to changes in blood glucose and with little to no pain.

SUMMARY

In some embodiments, the presently disclosed subject matter provides a composition comprising: (a) an amphiphilic polymeric material, wherein the amphiphilic polymeric material comprises a hydrophilic polymer conjugated to a hypoxia-sensitive hydrophobic group, wherein said hypoxia-sensitive hydrophobic group comprises a hypoxia-sensitive moiety that can be reduced in the presence of a hypoxic environment to form a hydrophilic moiety; (b) a diabetes treatment agent, optionally wherein the diabetes treatment agent is an insulin or a bioactive derivative thereof; and (c) a glucose oxidizing agent.

In some embodiments, the hydrophilic polymer is biodegradable. In some embodiments, the hydrophilic polymer is a polyamino acid, such as polyglutamic acid, a synthetic block copolymer, or a polysaccharide, optionally wherein the hydrophilic polymer is a polysaccharide, further optionally wherein the polysaccharide is a glucosaminoglycan. In some embodiments, the hydrophilic polymer is hyaluronic acid.

In some embodiments, the hypoxia-sensitive moiety comprises a nitroimidazole. In some embodiments, the hydrophobic group is covalently bound to the hydrophilic polymer. In some embodiments, the amphiphilic polymeric material comprises a hydrophilic polymer conjugated to an amino group of an amino-substituted hydrophobic group precursor, thereby forming an amide between said amino group and a carboxylic acid group present on the hydrophilic polymer. In some embodiments, the amphiphilic polymeric material comprises hyaluronic acid conjugated to 6-(2-nitroimidazole)hexylamine.

In some embodiments, the glucose oxidizing agent is glucose oxidase (GOx). In some embodiments, the diabetes treatment agent is an insulin or a bioactive derivative thereof, wherein the insulin or bioactive derivative thereof is selected from human insulin, a recombinant human insulin, insulin from a non-human animal, a fast-acting insulin, a rapid-acting insulin analog, an intermediate-acting insulin, and/or a long-acting insulin. In some embodiments, the diabetes treatment agent is recombinant human insulin. In some embodiments, the amphiphilic polymeric material forms a vesicle encapsulating said diabetes treatment agent and said glucose oxidizing agent.

In some embodiments, the presently disclosed subject matter provides a nanoparticle comprising: (a) an amphiphilic polymeric material, wherein the amphiphilic polymeric material comprises a hydrophilic polymer conjugated to a hypoxia-sensitive hydrophobic group, wherein said hypoxia-sensitive hydrophobic group comprises a hypoxia-sensitive moiety that can be reduced in the presence of a hypoxic environment to form a hydrophilic moiety; (b) a diabetes treatment agent, optionally an insulin or a bioactive derivative thereof; and (c) a glucose oxidizing agent.

In some embodiments, the presently disclosed subject matter provides a vesicle comprising an amphiphilic polymeric material comprising a hydrophilic polymer conjugated to a hypoxia-sensitive hydrophobic group, wherein said hypoxia-sensitive hydrophobic group comprises a hypoxia-sensitive moiety that is capable of reduction in a hypoxic environment to form a hydrophilic moiety, and further wherein (i) a diabetes treatment agent, optionally an insulin or a bioactive derivative thereof, and (ii) a glucose oxidizing agent are contained within said vesicle. In some embodiments, the hydrophilic polymer is a polyamino acid, such as polyglutamic acid, a synthetic block copolymer, or a polysaccharide, such as a glucosaminoglycan, optionally wherein the hydrophilic polymer is hyaluronic acid. In some embodiments, the hypoxia-sensitive moiety comprises a nitroimidazole. In some embodiments, the diabetes treatment agent is recombinant human insulin. In some embodiments, the glucose oxidizing agent is glucose oxidase (GOx).

In some embodiments, the presently disclosed subject matter provides a microneedle array comprising a vesicle comprising an amphiphilic polymeric material comprising a hydrophilic polymer conjugated to a hypoxia-sensitive hydrophobic group, wherein said hypoxia-sensitive hydrophobic group comprises a hypoxia-sensitive moiety that is capable of reduction in a hypoxic environment to form a hydrophilic moiety, and further wherein (i) a diabetes treatment agent, optionally an insulin or a bioactive derivative thereof, and (ii) a glucose oxidizing agent are contained within said vesicle. In some embodiments, the microneedle array comprises a plurality of microneedles wherein each of said plurality of microneedles has a length of between about 20 and about 1000 microns. In some embodiments, each of the plurality of microneedles has a length of about 600 microns.

In some embodiments, the microneedle array is provided as part of a skin patch, optionally wherein said patch comprises one or more backing layers and/or skin-compatible adhesives.

In some embodiments, the presently disclosed subject matter provides a closed-loop insulin delivery system comprising a microneedle array comprising a vesicle comprising an amphiphilic polymeric material comprising a hydrophilic polymer conjugated to a hypoxia-sensitive hydrophobic group, wherein said hypoxia-sensitive hydrophobic group comprises a hypoxia-sensitive moiety that is capable of reduction in a hypoxic environment to form a hydrophilic moiety, and further wherein (i) an insulin or a bioactive derivative thereof and (ii) a glucose oxidizing agent are contained within said vesicle.

In some embodiments, the presently disclosed subject matter provides a method of delivering a diabetes treatment agent to a subject in need thereof, the method comprising (a) providing a microneedle array comprising a vesicle comprising an amphiphilic polymeric material comprising a hydrophilic polymer conjugated to a hypoxia-sensitive hydrophobic group, wherein said hypoxia-sensitive hydrophobic group comprises a hypoxia-sensitive moiety that is capable of reduction in a hypoxic environment to form a hydrophilic moiety, and further wherein (i) a diabetes treatment agent, optionally an insulin or a bioactive derivative thereof, and (ii) a glucose oxidizing agent are contained within said vesicle, and (b) applying said array to a skin surface of said subject, wherein when glucose comes into contact with the microneedle array, it is oxidized, thereby creating a hypoxic environment that results in the reduction of the hypoxia-sensitive moiety to form a hydrophilic moiety, leading to disruption of vesicles and release of the diabetes treatment agent contained in the vesicles.

In some embodiments, the delivery of the diabetes treatment agent is at a rate corresponding to the glucose concentration coming into contact with the microneedle array. In some embodiments, the subject is a mammal. In some embodiments, the subject is diabetic.

In some embodiments, the presently disclosed subject matter provides a method of preparing a microneedle array for the glucose-sensitive delivery of a diabetes treatment agent, optionally an insulin or a bioactive derivative thereof, the method comprising: (a) preparing an aqueous solution of a vesicle comprising an amphiphilic polymeric material comprising a hydrophilic polymer conjugated to a hypoxia-sensitive hydrophobic group, wherein said hypoxia-sensitive hydrophobic group comprises a hypoxia-sensitive moiety that is capable of reduction in a hypoxic environment to form a hydrophilic moiety, and further wherein (i) a diabetes treatment agent, optionally an insulin or a bioactive derivative thereof, and (ii) a glucose oxidizing agent are contained within said vesicle; (b) dispersing said aqueous solution into a mold comprising a plurality of microneedle cavities, thereby providing a filled mold; (c) drying the filled mold to remove water; and (d) removing the mold to provide a microneedle array. In some embodiments, the method further comprises cross-linking polymeric materials in the microneedle array. In some embodiments, the cross-linking is performed by exposure to ultraviolet (UV) radiation.

In some embodiments, step (b) is performed under vacuum. In some embodiments, after step (b), the mold is centrifuged to compact the micelles into the microneedle cavities.

In some embodiments, prior to step (c), an additional hydrophilic polymer and/or a chemical cross-linker are added to the mold, optionally wherein the mold is centrifuged after the addition of the additional hydrophilic polymer and/or chemical cross-linker, further optionally wherein the additional hydrophilic polymer is a modified hyaluronic acid, such as an alkylene-modified and/or acrylate-modified hyaluronic acid. In some embodiments, step (c) is performed in a vacuum desiccator. In some embodiments, the mold comprises silicone.

Accordingly, it is an object of the presently disclosed subject matter to provide compositions, vesicles, nanoparticles, microneedles, microneedle arrays, systems, and methods for the glucose sensitive-delivery of a diabetes treatment agent, such as an insulin and/or a derivative thereof, as well as methods of preparing the microneedle arrays. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description of the presently disclosed subject matter and non-limiting Figures and Examples.

DETAILED DESCRIPTION

Figure 1A:
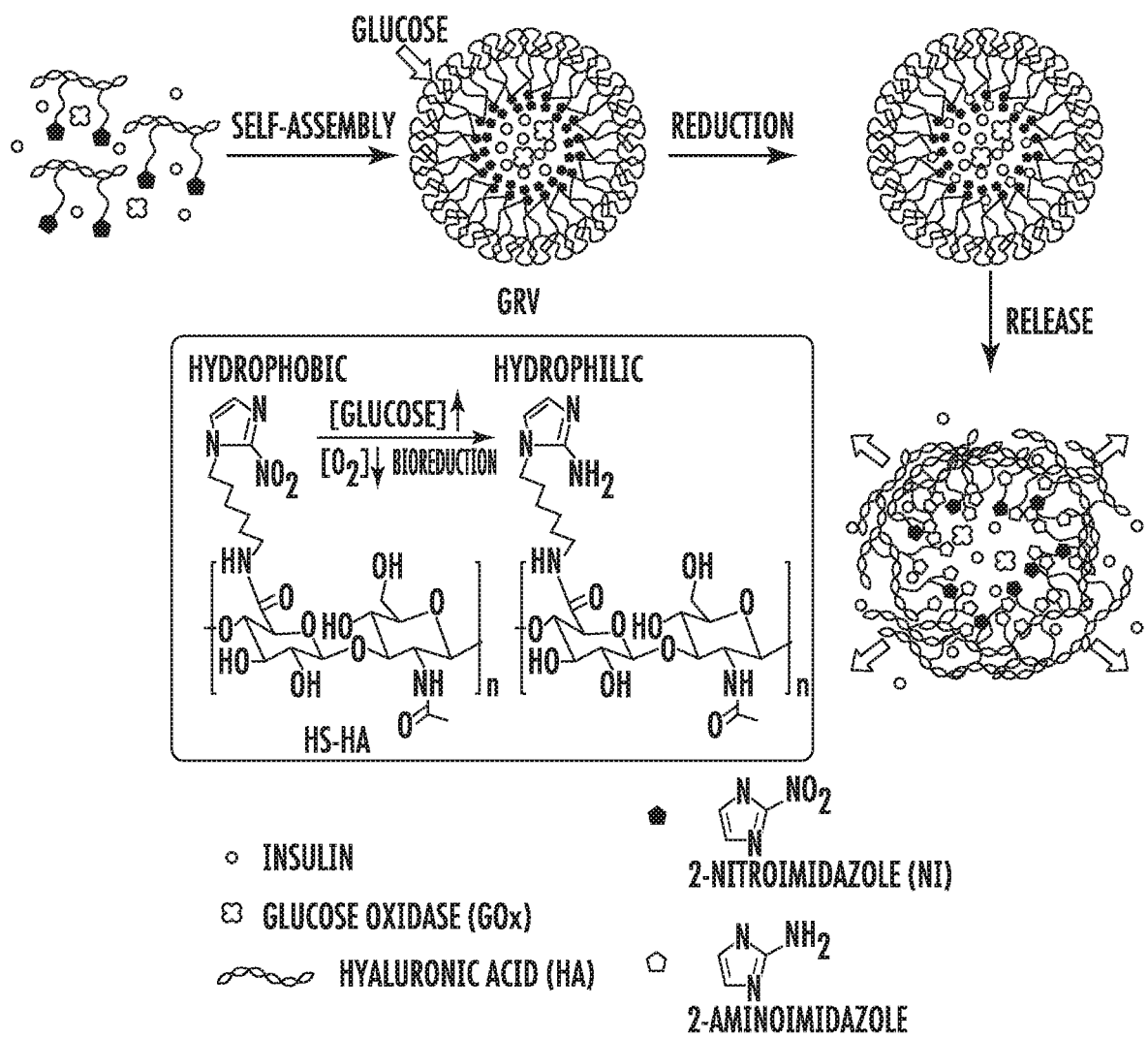
FIG. 1A is a schematic drawing showing the formation of a glucose-responsive insulin delivery system comprising a hypoxia-sensitive vesicle, also referred to herein as a glucose-responsive vesicle (GRV), prepared using hypoxia-sensitive (HS) hyaluronic acid (HA) and loaded with insulin and a glucose oxidizing enzyme, i.e., glucose oxidase (GOx); the reduction of a hydrophobic hypoxia-sensitive moiety, i.e., 2-nitroimidazole (NI), in the GRVs to form hydrophilic moieties (2-aminoimidazole) triggered by hypoxia caused by GOx oxidation of glucose; and the subsequent disassembly of the GRVs and release of insulin from the GRVs.

The presently disclosed subject matter will now be described more fully hereinafter with reference to the accompanying Figures and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art. Certain components in the figures are not necessarily to scale, emphasis instead being placed upon illustrating the principles of the presently disclosed subject matter (in some cases schematically).

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a composition" or "a polymer" includes a plurality of such compositions or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, or cyclic, saturated or at least partially or in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i,e., a $C_{1-8}$ alkyl), e.g., 1, 2, 3, 4, 5, 6, 7, or 8 carbon atoms, "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, nitro, amino, acylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aralkyl" refers to an -alkyl-aryl group, optionally wherein the alkyl and/or aryl group comprises one or more alkyl or aryl group substituents.

In some embodiments, the term "bivalent" refers to a group that can bond (e.g., covalently bond) or is bonded to two other groups, such as other alkyl, aralkyl, cycloalkyl, or aryl groups. Typically, two different sites on the bivalent group (e.g., two different atoms) can bond to groups on other molecules. For example, the bivalent group can be an alkylene group.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$(CH^2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

"Arylene" refers to a bivalent aryl group.

The term "amino" refers to the —NR'R" group, wherein R' and R" are each independently selected from the group including H and substituted and unsubstituted alkyl, cycloalkyl, heterocycle, aralkyl, aryl, and heteroaryl. In some embodiments, the amino group is —$NH_2$. "Aminoalkyl" and "aminoaryl" refer to the —NR'R" group, wherein R' is as defined hereinabove for amino and R" is substituted or unsubstituted alkyl or aryl, resectively.

The terms "carboxylate" and "carboxylic acid" can refer to the groups —C(═O)O⁻ and —C(═O)OH, respectively. In some embodiments, "carboxylate" can refer to either the —C(═O)O⁻ or —C(═O)OH group.

The term "amide" refers to a group having the formula —C(═O)—NRR", wherein R and R" are each independently H, alkyl, substituted alkyl, aralkyl, substituted aralkyl, aryl, or substituted aryl.

The terms "nanoscale," "nanomaterial," "nanometer-scale polymer" "nanocluster" and "nanoparticle" refer to a structure (e.g., a vesicle) having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is less than about 10 nm.

In some embodiments, the nanoparticle is approximately spherical. When the nanoparticle is approximately spherical, the characteristic dimension can correspond to the diameter of the sphere. In addition to spherical shapes, the nanoparticle or other nanoscale material can be disc-shaped, oblong, polyhedral, rod-shaped, cubic, or irregularly-shaped. A nanoscale material can also be irregularly shaped or comprise clusters of spheres, rods, discs, or cubes.

The term "micro" (e.g., in "microneedle") as used herein refers to a structure having at least one region with a dimension of less than about 1,000 microns (μm). In some embodiments, the term "micro" refers to a structure having a dimension between about 1 micron and about 1,000 microns.

The term "diameter" is art-recognized and is used herein to refer to either the physical diameter or the hydrodynamic diameter. The diameter of an essentially spherical particle can refer to the physical or hydrodynamic diameter. As used herein, the diameter of a non-spherical particle can refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Monodisperse" is used herein to describe a population of particles where all of the particles are the same or nearly the same size. For example, "monodisperse" can refer to particle distributions in which 90% of the distribution lies within 15%, 10% or 5% of the median particle size.

The terms "polymer" and "polymeric" refer to chemical structures that have repeating units (i.e., multiple copies of a given chemical substructure), As used herein, polymers can refer to groups having more than 10 repeating units and/or to groups wherein the repeating unit is other than methylene. Polymers can be formed from polymerizable monomers. A polymerizable monomer is a molecule that comprises one or more reactive moieties {e.g., siloxy ethers, hydroxyls, amines, vinylic groups (i.e., carbon-carbon double bonds), halides (i.e., Cl, Br, F, and I), esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as esters or amides, such that they can degrade overtime under biological conditions.

A "copolymer" refers to a polymer derived from more than one species of monomer.

As used herein, a "block copolymer" refers to a copolymer that comprises blocks (i.e., polymeric sub-sections of the whole copolymer) in a linear sequence. A "block" refers to a portion of a copolymer that has at least one feature that is not present in the adjacent portions of the macromolecule. Thus, a "block copolymer" can refer to a copolymer in which adjacent blocks are constitutionally different, i.e., each of these blocks comprises constitutional units derived from different characteristic species of monomer or with different composition or sequence distribution of constitutional units.

"Biocompatible" as used herein, generally refers to a material and any metabolites or degradation products thereof that are generally non-toxic to the recipient and do not cause any significant adverse effects to the recipient.

"Biodegradable" as used herein, generally refers to a material that will degrade or erode under physiologic conditions to smaller units or chemical species that are capable of being metabolized, eliminated, or excreted by the subject. In some embodiments, the degradation time is a function of polymer composition and morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks.

The term "hydrophilic" can refer to a group that dissolves or preferentially dissolves in water and/or aqueous solutions.

The term "hydrophobic" refers to groups that do not significantly dissolve in water and/or aqueous solutions and/or which preferentially dissolve in fats and/or non-aqueous solutions.

The term "amphiphilic" refers to a molecule or polymer that contains both hydrophilic and hydrophobic groups.

The terms "conjugate" and "conjugated" can refer to compositions that comprise at least two different chemical moieties or molecules (e.g., small molecules, polymers, proteins, etc.) bonded to one another, such as via ionic, coordinative or covalent bonds. In some embodiments, the term "conjugate" refers to moieties or molecules that are covalently bonded to one another. In some embodiments, the conjugate can comprise two different chemical moieties associated with one another via intermolecular forces such as hydrogen bonding, London dispersion forces, van der Waals' interactions, etc.

The term "insulin" as used herein refers to insulin from a human or other mammal. In some embodiments, the term "insulin" refers to human insulin. In some embodiments, the term "insulin" refers to recombinant human insulin.

"Bioactive derivative" as used herein refers to human insulin or another mammalian insulin in which one or more amino acid residues have been replaced by another amino acid residue or deleted, in which the A chain and/or the B chain has been extended by addition of one or more amino acid residues at the N-terminal or at the C-terminal, and/or in which the insulin has been modified by the addition of one or more chemical substituents. The derivative can function to replace endogenous insulin and retains at least some of the biological activity of endogenous insulin. Insulin derivatives can have different pharmacokinetics than endogenous insulin. Dosages can be optimized based on the pharmacokinetics of the insulin derivative relative to human insulin based on known pharmacokinetics by one of skill in the art.

The term "diabetes treatment agent" as used herein can refer to a therapeutic agent that treats diabetes or a complication thereof (such as, but not limited to, diabetic neuropathy, diabetic retinopathy, diabetic nephropathy, glaucoma, and diabetic ketoacidosis) or another glucose metabolism disorder that results in hyperglycemia. In some embodiments, the diabetes treatment agent is an insulin or a bioactive derivative thereof or a non-insulin-based treatment agent known in the art for use in the treatment of diabetes. Suitable non-insulin-based treatment agents for use in the treatment of diabetes include, but are not limited to, insulin sensitizers, DPP IV inhibitors, glucagon-like peptide 1 (GLP-1) and analogs thereof, insulin secretagogues, such as, but not limited to sulfonylureas, meglitinides, gastric inhibitory polypeptide (GIP), insulin receptor activators, biguanides, thiazolidinediones, alpha-glucosidase inhibitors, and the like. In some embodiments, the diabetes treatment agent is an insulin or a bioactive derivative.

The terms "cross-linking reagent" or "cross-linking agent" refer to a compound that includes at least two reactive functional groups (or groups that can be deblocked or deprotected to provide reactive functional groups), which can be the same or different. In some embodiments, the two reactive functional groups can have different chemical reactivity (e.g., the two reactive functional groups are reactive (e.g., form bonds, such as covalent bonds) with different types of functional groups on other molecules, or one of the two reactive functional groups tends to react more quickly with a particular functional group on another molecule than the other reactive functional group). Thus, the cross-linking reagent can be used to link (e.g., covalently bond) two other entities (e.g., molecules, polymers, proteins, nucleic acids, vesicles, liposomes, nanoparticles, microparticles, etc.) to form a cross-linked composition.

The term "vesicle" can refer to an artificially created particle, (in some embodiments, a nanoparticle) comprising fluid enclosed by a concentric layer or layers of a molecule or polymer (e.g., an amphiphilic polymer). Dissolved or suspended in the fluid can be one or more therapeutic agents (e.g., small molecules, proteins, nucleic acids, etc.). According to some embodiments of the presently disclosed subject matter, the fluid can comprise a diabetes treatment agent, such as an insulin or bioactive derivative thereof, and a glucose oxidizing agent, such as glucose oxidase, dissolved in an aqueous solution. The fluid can comprise more than one therapeutic agent, e.g., both insulin or bioactive derivative thereof and another therapeutic agent, such as non-insulin-based agent for treating diabetes or a complication thereof. In some embodiments, each therapeutic agent can be a water-soluble therapeutic agent.

The term "hyperglycemia", as used herein, can refer to a condition in which an elevated amount of glucose circulates in the blood plasma of a subject relative to a healthy individual. Hyperglycemia can be diagnosed using methods known in the art, including measurement of fasting blood glucose levels.

The term "hyperinsulinemia", as used herein, can refer to a condition in which there are elevated levels of circulating insulin when, concomitantly, blood glucose levels are either elevated or normal. Hyperinsulinemia can be caused by insulin resistance associated with dyslipidemia, such as high triglycerides, high cholesterol, high low-density lipoprotein (LDL) and low high-density lipoprotein (HDL); high uric acids levels; polycystic ovary syndrome; type II diabetes and obesity.

The term "insulin resistance" as used herein can refer to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" as used herein can refer to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and/or other disorders (e.g., atherosclerosis).

The term "glucose tolerance," as used herein, can refer to the ability of a subject to control the level of plasma glucose and/or plasma insulin when glucose intake fluctuates. For example, glucose tolerance encompasses the ability to reduce the level of plasma glucose back to a level before the intake of glucose within about 120 minutes or so.

II. General Considerations

An artificial pancreas-like closed-loop glucose-responsive insulin delivery system that is able to "secrete" insulin in response to elevated blood glucose could provide a desirable way of regulating glycemia with minimal patient effort and potential improvements in glycemia and quality of life. See Bratlie et al., Advanced Healthcare Materials, 1(3):267-284 (2012); Ravaine et al., J. Controlled Release, 132(1):2-11 (2008); and Wu et al., Chem. Rev., 111(12): 7855-7875 (2011). Current closed-loop systems combine a glucose monitoring module and a sensor-triggered insulin releasing module. See Bratlie et al., Advanced Healthcare Materials, 1(3):267-284 (2012); and Ravaine et al., J. Controlled Release, 132(1):2-11 (2008). For example, there are closed-loop electronic/mechanical devices which employ a continuous glucose-monitoring sensor calibrated by the patient and an external insulin infusion pump. See Veiseh et al., Nature Reviews Drug Discovery, 14(1):45-57 (2015). However, various challenges, such as guaranteeing accurate signal feedback and preventing biofouling, can be associated with such devices.

One way to avoid some of these challenges involves a chemical approach that utilizes an insulin-loaded matrix having glucose-sensing elements. The matrix could be designed to undergo structural transformations, e.g., shrinking, swelling, or dissociation, in response to glucose concentration changes, leading to a glucose-stimulated insulin release. See Gordijo et al., Adv. Funct. Mater., 21(1):73-82 (2011); Gu et al., ACS Nano, 7(8):6758-6766 (2013); Katoaka et al., J. Am. Chem. Soc., 120(48):12694-12695 (1998); and Gu et al., ACS Nano, 7(5):4194-4201 (2013). Possible glucose-sensing moieties for synthetic closed-loop devices include phenylboronic acid (PBA), glucose-binding protein (GBP), and glucose oxidase (GOx). Unfortunately, the majority of existing synthetic closed-loop systems have been limited to in vitro studies, with relatively few showing applicability in vivo due to particular issues related to each glucose-sensing strategy. For instance, PBA and its derivatives are known for reversible interaction with polyol molecules, such as glucose (see Aronoff et al., Carbohydr. Res., 40(2):299-309 (1975)); but efficient interaction between glucose and PBA and a subsequent structural change of the matrix usually requires a basic pH, higher than the physiological environment. The safety and toxicity of PBA conjugates also remain to be established. Concanavalin A (Con A) is the most commonly used GBP for insulin delivery, generally based on its multiple binding sites and competitive interaction with glucose and dextran (used as the matrix material). See Kim et al., J. Controlled Release, 11(1):193-201 (1990). However, the in vivo toxicity and instability of Con A limits its clinical applications. See Tiegs et al., J. Clin. Invest., 90(1):196 (1992).

GOx is an enzyme which can convert glucose to gluconic acid in the presence of oxygen:

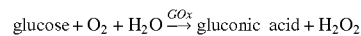

See Wu et al., Chem. Rev., 111(12):7855-7875 (2011). Glucose-responsive systems employing GOx have previously been integrated with pH-sensitive materials, which can be either protonated or degraded with a local decrease of pH, promoted by increasing glucose concentration. Yet, such pH decrease-dependent methods can be compromised by slow responsiveness, especially in a buffered physiologic environment. See Veiseh et al., Nature Reviews Drug Discovery, 14(1):45-57 (2015).

The presently disclosed subject matter provides a method of delivering insulin that combines: (1) fast responsiveness, to better mimic the pharmacokinetics to normal pancreatic activity; (2) ease of administration; and (3) biocompatibility without long-term side effects. More particularly, the presently disclosed subject matter provides delivery devices for insulin (and/or other diabetes treatment agents) based on hypoxia-sensitive vesicles containing (e.g., dissolved in a fluid enclosed in the vesicle) insulin (and/or another diabetes treatment agent) and a glucose oxidizing agent (e.g., GOx). Instead of utilizing enzymatically induced pH changes, the presently disclosed devices take advantage of the local generation of hypoxia due to the consumption of oxygen during the oxidation of glucose as a trigger for rapidly promoting release of insulin (and/or another diabetes treatment agent) in response to hyperglycemia. The transport coefficient of oxygen has been demonstrated to be slower than the diffusion coefficient of hydrogen ion in vivo (see Fletcher, Biophys. J., 29(3):437-458 (1980); Michaels et al. AICHE J., 21(5):985-996 (1975); and Dowd et al., Journal of Bone and Joint Surgery, British Volume, 65(1):79-83 (1983)), which implies that a faster response could be achieved if hypoxia-sensitive materials are incorporated in glucose oxidizing agent-based glucose-responsive formulations.

In one embodiment of the presently disclosed subject matter, to achieve hypoxia-responsive transduction, 2-nitroimidazole (NI)-modified materials were used as a hypoxia-sensitive material. NI is a hydrophobic component that is often utilized in cancer imaging due to its high sensitivity to the hypoxic condition in tumor sites. See Nunn et al., Eur. J. Nucl. Med., 22(3):265-280 (1995); and Krohn et al., J. Nucl. Med., 49(Suppl. 2):129S-148S (2008). NI can be converted to hydrophilic 2-aminoimidazole in a hypoxic environment via a single-electron reduction catalyzed by a series of nitroreductases, coupled to a bio-reducing agent, such as nicotinamide adenine dinucleotide phosphate (NADPH), a coenzyme that is plentiful in biological tissues. See Nunn et al., Eur. J. Nucl. Med., 22(3):265-280 (1995); Krohn et al., J. Nucl. Med., 49(Suppl. 2):129S-148S (2008); Edwards, J. Antimicrob. Chemother., 31(1):9-20 (1993); and Takasawa et al., Stroke, 39(5):1629-1637 (2008), (25-28).

As shown in FIG. 1A, amine-functionalized NI was conjugated to a biocompatible, biodegradable polymer, hyaluronic acid (HA; molecular weight: 300 kDa). Through self-assembly, the amphiphilic hypoxia-sensitive HA (HS-HA) can readily form nanoscale glucose-responsive vesicles (GRVs), which can encapsulate recombinant human insulin (and/or another diabetes treatment agent) and a glucose oxidizing agent, such as GOx, in an aqueous solution. In the presence of high blood glucose, dissolved oxygen can be rapidly consumed due to the glucose oxidation catalyzed by the glucose oxidizing agent, which leads to a local hypoxic environment. NI groups on the HS-HA are then reduced into hydrophilic 2-aminoimidazoles in the presence of NADPH and reductase, which results in the dissociation of GRVs and subsequent release of insulin (and/or other diabetes treatment agent).

Figure 1B:
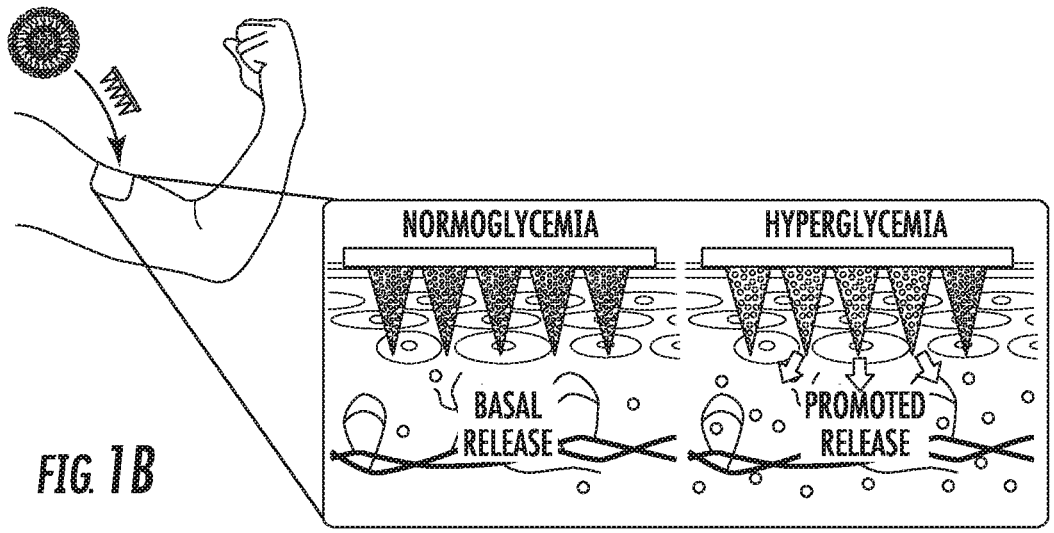
FIG. 1B shows schematic drawings of a glucose-response vesicle (GRV)-containing microneedle array patch for in vivo insulin delivery triggered by a hyperglycemic state. The microneedles can comprise the GRVs described for FIG. 1A and the patch can be applied to the skin. Under a normoglycemia state, little insulin is released; but under a hyperglycemic state, insulin release from the microneedles is triggered.
Figure 4A:
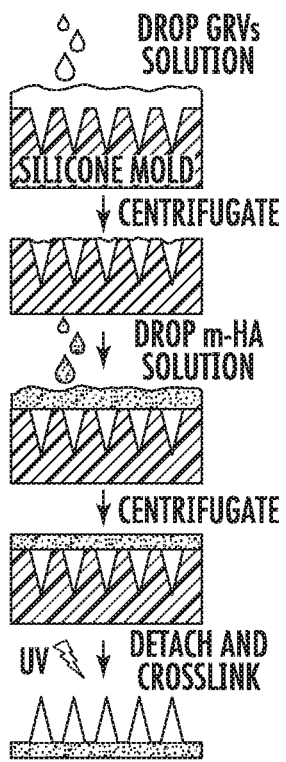
FIG. 4A is a schematic drawing of an exemplary fabrication process for glucose-responsive vesicle (GRV)-loaded microneedle (MN) array patches of the presently disclosed subject matter from a silicone mold.

To increase ease of administration, the presently disclosed GRVs can be loaded into a microneedle (MN) array-based patch for painless delivery of a diabetes treatment agent (e.g., insulin). See FIGS. 1B and 4A. For instance, as shown in FIG. 4A, a matrix of microneedles can be made from crosslinked HA, where the cross-linking can improve the stiffness of microneedles and restrict loss of GRVs from needles. As shown in FIG. 1B, upon subcutaneous administration, the GRVs loaded in the microneedles disassemble when exposed to a high interstitial fluid glucose level in vascular and lymph capillary networks, thereby promoting the release of the diabetes treatment agent (e.g., insulin) which can be taken up through the regional lymph and capillaries vessels quickly. As described hereinbelow, an exemplary "smart insulin patch" with a hypoxia-sensitive, glucose-responsive mechanism can display rapid glucose-regulation responsiveness and reliable avoidance of hypoglycemia in a mouse model of type 1 diabetes.

III. Glucose-Responsive Vesicles, Related Compositions and Systems

A closed-loop insulin delivery system that "secretes" insulin in response to blood glucose holds vast promise for treating type 1 and advanced type 2 diabetes and improving the quality of life for diabetic patients. The presently disclosed subject matter provides, in some embodiments, a glucose-responsive delivery device for delivery of insulin and/or another diabetes treatment agent using a painless microneedle-array patch containing hypoxia-sensitive vesicles, which can be quickly dissociated and release an encapsulated therapeutic agent or agents (e.g., insulin) when exposed to a local hypoxic environment generated by the enzymatic oxidation of glucose in the hyperglycemic state. This "smart insulin patch" can regulate the blood glucose with fast responsiveness and the avoidance of hypoglycemia.

In some embodiments, the presently disclosed subject matter relates to compositions for the delivery of a diabetes treatment agent (e.g., insulin or bioactive derivatives thereof) to a subject in need thereof, e.g., for the control of diabetes or another glucose metabolism disorder that leads to hyperglycemia. In some embodiments, the presently disclosed compositions can provide glucose-sensitive closed-loop diabetes treatment agent delivery to a subject in need thereof, thereby providing for more cost-effective and easier control of diabetes, as well as for the prevention of hypoglycemic complications of the treatment of diabetes.

In some embodiments, the presently disclosed subject matter provides a composition comprising:
(a) an amphiphilic polymeric material, wherein the amphiphilic polymeric material comprises a hydrophilic polymer conjugated to a hypoxia-sensitive hydrophobic group, wherein the hypoxia-sensitive hydrophobic group comprises a hypoxia-sensitive moiety that can be reduced in the presence of a hypoxic environment to form a hydrophilic moiety;
(b) a diabetes treatment agent, optionally an insulin or a bioactive derivative thereof; and
(c) a glucose oxidizing agent.

The hydrophilic polymer can be a synthetic or a naturally-occurring biocompatible polymer. Suitable hydrophilic polymers can include polar or charged side chain moieties. In some embodiments, the hydrophilic polymer can be biodegradable. Suitable hydrophilic polymers include, but are not limited to polyamine acids (such as polyglutamic acid, polyaspartic acid, etc.) synthetic block copolymers (e.g., wherein at least one block comprises a hydrophilic polymeric chain), and polysaccharides, such as glucosaminoglycans (GAGS). In some embodiments, the hydrophilic polymer is a GAG, such as hyaluronan or hyaluronic acid; heparin, heparan sulfate, chondroitin sulfate, dermatan sulfate, and keratin sulfate. In some embodiments, the hydrophilic polymer is hyaluronic acid.

As indicated above, the hydrophobic group comprises a hypoxia-sensitive moiety, for example a moiety that can undergo a chemical reaction or other structural change in response to a decrease in oxygen (e.g., in a solvent or physiological environment in contact with the amphiphilic polymeric material). For example, the hypoxia-sensitive group can undergo a reduction reaction or reactions in response to a decrease in oxygen. The reduction reaction or reactions can be catalyzed by an enzyme. In some embodiments, the decrease in oxygen can be the result of the localized depletion of oxygen caused by the activity of a glucose oxidizing agent that oxidizes glucose in contact with the amphiphilic polymeric material. Thus, in some embodiments, the hypoxia is a side effect of an increase in glucose concentration near the amphiphilic polymeric material and its associated glucose oxidizing agent.

Representative hypoxia-sensitive moieties include nitro-substituted aryl groups. In some embodiments, the hypoxia-sensitive moiety is a nitroimidazole (e.g, a 2-nitroimidazole). The nitroimidazole can comprise one or more aryl group substituents (e.g., alkyl, halo, etc.) substituted on carbon and/or nitrogen atoms of the imidazole ring, i.e., in addition to the nitro group substituted on the imidazole ring. In some embodiments, the hypoxia-sensitive moiety can include more than one nitro group.

In some embodiments, the hydrophobic group is covalently bound to the hydrophilic polymer. For example, the hydrophobic group can be based on a precursor molecule that includes an amino group. The amino group of the precursor molecule can form an amide linkage with a carboxylic acid group present on the hydrophilic polymer. In some embodiments, the amphiphilic polymeric material can comprise hyaluronic acid (or another hydrophilic polymer that comprises carboxylic side chain groups) conjugated to a 2-nitroimidazole-substituted alkylamine, such as, but not limited to 6-(2-nitroimidazole)hexylamine, 5-(2-nitroimidazole)pentylamine, 4-(2-nitroimidazole)butylamine, 7-(2-nitroimidazole)heptylamine, 8-(2-nitroimidazole)octylamine, and the like.

Any suitable glucose oxidizing agent can be used. In some embodiments, the glucose oxidizing agent is an enzyme, such as glucose oxidase (GOx) (EC1.1.3.4), which oxidizes glucose to produce hydrogen peroxide and D-glucono-δ-actone, the cyclic form of gluconic acid. In some embodiments, the glucose oxidizing agent can be a biologically active variant of GOx.

In some embodiments, the diabetes treatment agent is an insulin or bioactive derivative thereof, such as human insulin, recombinant human insulin, insulin from a non-human animal source (e.g. bovine, porcine) or any other insulin, including insulin derivatives. In some embodiments, the insulin is of the same species as the intended recipient, i.e., human insulin for treatment of humans. The insulin or bioactive derivative thereof can include mixtures of different insulins and/or derivatives. The insulin or bioactive derivative thereof can include fast-acting insulins, rapid-acting insulin analogs, intermediate-acting insulins, and/or long-acting insulins. In some embodiments, the insulin or bioactive derivative thereof is a fast-acting or rapid-acting insulin.

Fast-acting insulins start to work within one to 20 minutes, peaking about one hour later and lasting from three to five hours. Fast-acting insulin takes about two hours to fully absorb into the systemic circulation. Fast-acting insulins include regular recombinant human insulin (such as HUMULIN™ marketed by Lilly, and NOVOLIN™, marketed by NovoNordisk). Bovine and porcine insulins, which differ in several amino acids to human insulin, but are bioactive in humans, are also fast acting insulins.

Rapid-acting insulins include insulins that have been modified or have altered locations of amino acids in order to enhance their rate of absorption. There are three types of rapid-acting commercial insulin analogs available: lispro insulin (Lysine-Proline insulin, sold by Eli Lilly as HUMALOG™), glulisine insulin (sold by Sanofi-Aventis as APIDRA™) and aspart insulin (sold by Novo Nordisk as NOVOLOG™).

Intermediate-acting insulin has a longer lifespan than short-acting insulin, but it is slower to start working and takes longer to reach its maximum strength. Intermediate-acting insulin usually starts working within 2-4 hours after injection, peaks somewhere between 4-14 hours after injection, and remains effective up to 24 hours after injection. Types of intermediate-acting insulin include NPH (Neutral Protamine Hagedorn) and LENTE™ insulin. NPH insulin contains protamine which slows down the speed of absorption so that the insulin takes longer to reach the bloodstream but has a longer peak and lifespan.

Long-acting insulins include Eli Lilly's Humulin™ U (Ultralente™ human insulin (recombinant DNA origin) extended zinc suspension); and insulin glargine (LANTUS™ Aventis). Insulin glargine is a recombinant human insulin analog that can have up to 24 hour duration. It differs from human insulin by having a glycine instead of asparagine at position 21 and two arginines added to the carboxy-terminus of the beta-chain. LANTUS™ consists of insulin glargine dissolved in a clear aqueous fluid (100 IU, 3.6378 mg insulin glargine, 30 micrograms zinc, 2.7 mg m-cresol, 20 mg glycerol 85%, and water to 1 mL).

Additionally, or as an alternative to the insulin or bioactive derivative thereof, the presently disclosed composition can comprise a non-insulin-based active agent known in the art for the treatment of diabetes or for a complication thereof or for another glucose metabolism disorder. Thus, in some embodiments, the presently disclosed composition can include a non-insulin-based diabetes drug, such as, but not limited to, the non-insulin-based diabetes treatment agents listed hereinbelow, e.g., glucogon-like peptide 1 (GLP1) or an analog thereof, an alpha-glucosidase inhibitor, a sulfonylurea, a thiazolidinedione, or a biguanide.

In some embodiments, the amphiphilic polymeric material forms a nanoparticle that contains the diabetes treatment agent (e.g., the insulin or bioactive derivative thereof and/or other diabetes treatment agent) and the glucose oxidizing agent enclosed or entrapped within the interior of the nanoparticle (e.g., in pores or other interior spaces within the nanoparticle) or otherwise non-covalently associated with the polymeric material. In some embodiments, reduction of the hypoxia-sensitive moiety can disrupt the nanoparticle structure (e.g., as the amphiphilic polymer becomes more hydrophilic), allowing the diabetes treatment agent (e.g., the insulin or bioactive derivative thereof) to be dispersed from the nanoparticle (e.g., by diffusion). In some embodiments, the amphiphilic polymeric material forms a vesicle encapsulating the diabetes treatment agent (e.g., the insulin or bioactive derivative thereof) and the glucose oxidizing agent. Reduction of the hypoxia-sensitive moiety (e.g., in response to hypoxia resulting from an increase in activity of the glucose oxidizing agent due to an increase in glucose) can lead to disassembly of the vesicle and release of the diabetes treatment agent (e.g., the insulin or derivative thereof).

In some embodiments, the nanoparticles and/or vesicles have an average diameter of between about 50 to about 500 nm. In some embodiments, the average diameter is between about 50 and about 250 nm. In some embodiments, the average diameter is between about 80 and about 160 nm (e.g., about 80, 85, 90, 95, 100, 105, 110, 115, 120, 125, 130, 135, 140, 145, 150, 155, or 160 nm). In some embodiments, the nanoparticles and/or vesicles have an average diameter (e.g., as measured via dynamic light scattering) of about 118 nm. In some embodiments, the nanoparticles and/or vesicles can be mono-disperse or nearly mono-disperse (e.g., wherein at least about 80% of the distribution lies within 15%, 10% or 5% of the median particle size).

In some embodiments, the compositions of the presently disclosed subject matter, e.g., the nanoparticles and/or vesicles, can be used to prepare a microneedle or microneedle array for the delivery of a diabetes treatment agent (e.g., insulin or of a bioactive derivative thereof).

In some embodiments, the presently disclosed subject matter provides a microneedle array comprising a plurality of microneedles comprising vesicles and/or nanoparticles, wherein the vesicles and/or nanoparticles comprise an amphiphilic polymeric material comprising a hydrophilic polymer conjugated (e.g., covalently conjugated) to a hypoxia-sensitive hydrophobic group, wherein said hypoxia-sensitive hydrophobic group comprises a hypoxia-sensitive moiety that is capable of reduction in a hypoxic environment to form a hydrophilic moiety, and further wherein (i) a diabetes treatment agent, optionally an insulin or a bioactive derivative thereof, and (ii) a glucose oxidizing agent are contained within said vesicle. In some embodiments, the microneedle array can comprise a plurality of microneedles wherein each of said plurality of microneedles has a length of between about 20 and about 1000 microns (e.g., about 20, 50, 100, 150, 200, 250, 300, 350, 400, 450, 500, 550, 600, 650, 700, 750, 800, 850, 900, 950, or about 1000 microns). In some embodiments, each of the plurality of microneedles has a length of between about 500 microns and about 700 microns. In some embodiments, each microneedle can have an approximately conical or pyramidal shape. In some embodiments, the tip of the microneedles can be less than about 100 microns, less than about 75 microns, less than about 50 microns, less than about 40 microns, less than about 30 microns, or less than about 20 microns. In some embodiments, the tip of each of the microneedles can be about 10 microns.

The microneedle array can comprise a plurality of microneedles, wherein the bases of microneedles are arranged in any suitable two-dimensional pattern. The microneedles can be arranged in a regular array (e.g., a square, rectangular, circular, oval or other shaped pattern) wherein the distance between individual microneedles remains the same or varies in a repeating fashion, or in an irregular array (e.g., wherein the distance between individual microneedles varies in no recognizable repeating fashion).

In some embodiments, the microneedle array can be provided as part of a skin patch. In some embodiments, the microneedle array can comprise one or more backing layers (e.g., to protect the microneedle array from moisture or physical insult (e.g., scratches). In some embodiments, the microneedle array can comprise a layer that extends outward from the array (e.g., coplanar to the base of the array) that comprises a skin-compatible adhesive for aiding in the attachment of the array to the skin.

The presently disclosed microneedle arrays can release a diabetes treatment agent or agents (e.g., insulin or a bioactive derivative thereof and/or another diabetes treatment agent) in a glucose-responsive or dependent manner. In some embodiments, the release rate of the diabetes treatment agent or agents (e.g., of the insulin or bioactive derivative) is dependent upon the concentration of glucose coming into contact with the array (e.g., the release rate is faster when the array in in contact with higher concentrations of glucose). In some embodiments, the microneedle array is a closed-loop insulin delivery system.

IV. Methods of Treatment

In some embodiments, the presently disclosed subject matter provides a method of delivering a diabetes treatment agent, such as insulin or a bioactive insulin derivative, to a subject in need thereof, the method comprising administering a composition (e.g., a nanoparticle and/or vesicle) of the presently disclosed subject matter to the subject. The administration can by any suitable route (e.g., oral, intravenous (i.v.), intraperitoneally (i.p.), sub-cutaneous, intramuscular, transdermal, or via inhalation). The presently disclosed compositions can be provided in a therapeutically effective amount in any suitable pharmaceutically acceptable carrier (e.g., water), vehicle or diluent.

By "therapeutically effective amount" is meant that the administration of that amount to an individual, either in a single dose, or as part of a series of doses, is effective to produce a measurable effect on the subject. For example, a therapeutically effective amount can be the amount required to lower or reduce the blood glucose concentration of the subject or to cause an improvement in a glucose tolerance test. Thus, a therapeutically effective amount can be an amount sufficient to reduce or decrease any level (e.g., a baseline level) of fasting plasma glucose (FPG), wherein, for example, the amount is sufficient to reduce a FPG level greater than 200 mg/dL to less than 200 mg/dL or wherein the amount is sufficient to reduce a FPG level between about 175 mg/dL and about 200 mg/dL to less than the starting level. In some embodiments, the therapeutically effective amount is an amount sufficient to reduce the FPG level to less than about 150 mg/dL, less than about 125 mg/dL, less than about 120 mg/dL, less than about 115 mg/dL, or less than about 110 mg/dL. The therapeutically effective amount can be adjusted in connection with dosing regimen and diagnostic analysis of the subject's condition (e.g., monitoring levels of glucose and/or insulin in the plasma). The therapeutically effective amount can vary depending upon the health and physical condition of the subject, the subject's weight, the degree of disease resolution desired, the activity of the insulin or insulin derivative (or other diabetes treatment agent), the activity of the glucose oxidizing agent, the formulation, etc.

In some embodiments, the method comprises providing a microneedle array of the presently disclosed subject matter, and applying said array to a skin surface of the subject. When glucose comes into contact with the microneedle array, it is oxidized, thereby creating a hypoxic environment that results in the reduction of the hypoxia-sensitive moiety of the hydrophobic group of the amphiphilic polymeric material, thereby forming a hydrophilic moiety. Formation of the hydrophilic moiety can lead to disruption of the vesicles and/or nanoparticles comprising the amphiphilic polymeric material and the release of the diabetes treatment agent (e.g., the insulin or bioactive insulin derivative) contained in the vesicles and/or nanoparticles. In some embodiments, the delivery of the diabetes treatment agent (e.g., the insulin or bioactive insulin derivative) is at a rate corresponding to the glucose concentration coming into contact with the microneedle array.

In some embodiments, more than one microneedle array can be applied to a skin surface of the subject, e.g., simultaneously or sequentially. For example, microneedle arrays can be applied sequentially every few hours. In some embodiments, one or more arrays can be applied prior to, during, or within a few minutes (e.g., within about 5 to about 120 minutes) after the consumption of food by the subject. In some embodiments, an array is applied prior to consumption of food by the subject and a second array is applied within a few minutes after consumption of food by the subject.

The microneedle array can include a suitable unit dosage of diabetes treatment agent (e.g., insulin or bioactive derivative thereof) appropriate for the subject being treated (e.g., based on the subject's weight) and/or based upon an actual or expected blood glucose concentration in the subject being treated (e.g., based upon actual or expected food intake (particularly carbohydrate intake) by the subject). The term "unit dosage" can refer to a discrete unit containing a predetermined quantity of insulin, glucose oxidizing agent and/or other therapeutic agent, sufficient to produce a desired or measurable effect.

In some embodiments, one or more additional therapeutic agent is contained within the vesicles and can be released along with the diabetes treatment agent (e.g., the insulin or bioactive derivative thereof). In some embodiments, the additional therapeutic agent is water-soluble. In some embodiments, the additional therapeutic agent is a protein or protein derivative.

In some embodiments, the vesicle can include both insulin (or a bioactive derivative thereof) and an additional therapeutic agent, wherein the additional therapeutic agent is another agent for treating diabetes or a complication thereof (e.g., diabetic neuropathy, diabetic retinopathy, diabetic nephropathy, glaucoma, diabetic ketoacidosis, bacterial or fungal infections). For instance, in some embodiments, the additional therapeutic agent can include one or more non-insulin-based active agents known in the art and used in the treatment of diabetes (e.g., type-2 diabetes). The non-insulin-based diabetes agents can fall within several broad classes of drugs including, but not limited to, insulin sensitizers, DPP IV inhibitors, and GLP1 analogs, insulin secretagogues including, but not limited to, sulfonylureas such as acetohexamide (DYMELOR), chlorpropamide (DIABINESE), tolazamide (TOLINASE), tolbutamide (ORINASE), glimepiride (AMARYL), glipizide (GLUCOTROL), glipizide extended release (GLUCOTROL XL), glyburide (DIABETA, MICRONASE), glyburide micronized (GLYNASE, PRESTAB), meglitinides such as nateglinide (STARLIX) and repaglinide (PRANDIN), gastric inhibitory polypeptide (GIP), glucagon-like peptide (GLP)-1, morphilinoguanide BTS 67582, phosphodiesterase inhibitors, and succinate ester derivatives, insulin receptor activators; insulin sensitizing biguanides such as metformin (GLUCOPHAGE), thiazolidinediones (TZD) such as troglitazone (REZULIN), pioglitazone (ACTOS), roziglitazone (AVANDIA), MCC-555, rivoglitazone, ciglitazone; non-TZD peroxisome proliferator activated receptor-γ (PPAR-γ) agonist GL262570, alpha-glucosidase inhibitors such as acarbose (PRECOSE) and miglitol (GLYSET), combination agents such as glucovance (GLUCOPHAGE with GLYBURIDE), tyrosine phosphatase inhibitors such as vanadium, PTP-1B inhibitors, and AMPK activators, including 5-aminoimidazole-4-carboxamide ribonucleoside (AICAR), and other agents such as exendin (EXENATIDE (synthetic exendin-4)) and amylin (SYMLIN™ (pramlintide acetate)), D-chiro-inositol, altered peptide ligands (NBI-6024), anergix DB complex, GABA inhibit melanocortin, glucose lowering agent (ALT-4037), aerodose (AEROGEN), insulin mimics, insulin-like growth factor-1 alone or in a complex with BP3 (SOMATOKLINE), metoclopramide HCL (Emitasol/SPD 425), motillde/erythromycin analogs, and GAG mimetics. In certain embodiments, the non-insulin-based diabetes treatment agent can be an insulin sensitizer, such as, but not limited to, a thiazolidinedione, for example, rosiglitazone, pioglitazone, troglitazone, MCC-555, rivoglitazone, ciglitazone, and the like, and combinations thereof.

In some embodiments, the subject treated according to the presently disclosed subject matter is a human subject, although it is to be understood that the methods described herein are effective with respect to all vertebrate species, which are intended to be included in the term "subject."

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock, including, but not limited to, domesticated swine (pigs and hogs), ruminants, horses, poultry, and the like.

Generally, the presently disclosed methods can be used to treat subjects with diabetes or another glucose metabolism disorder that results in increased blood glucose concentration (i.e., hyperglycemia). The phrase "glucose metabolism disorder" can encompass any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, other metabolic disorders (such as metabolic syndrome, which is also referred to as syndrome X), and obesity, among others.

Broadly speaking, the terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" as used herein can refer to a state wherein a subject does not have the characteristics, symptoms, and the like typically observed in diabetes, but does have characteristics, symptoms and the like that, if left untreated, may progress to diabetes. The presence of these conditions may be determined using, for example, either the fasting plasma glucose (FPG) test or the oral glucose tolerance test (OGTT). Both usually require a subject to fast for at least 8 hours prior to initiating the test.

In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dL, a subject with "pre-diabetes" would generally have a FPG concentration between about 100 and about 125 mg/dL, and a subject with "diabetes" would generally have a FPG level above about 126 mg/dL.

In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dL, a pre-diabetic subject generally has a blood glucose concentration about 140 to about 199 mg/dL, and a diabetic subject generally has a blood glucose concentration about 200 mg/dL or above.

While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dL, a murine subject with "pre-diabetes" would generally have a FPG concentration between about 175 and about 250 mg/dL and a murine subject with "diabetes" would generally have a FPG concentration above about 250 mg/dL.

In some embodiments, the subject is diabetic. The subject can have type 1 or type 2 diabetes. In some embodiments, the subject can have gestational diabetes or pre-diabetes. In some embodiments, the subject can have a glucose metabolism disorder other than diabetes (e.g., metabolic syndrome, impaired glucose metabolism, hyperinsulinemia, etc.). Suitable candidates for treatment using the presently disclosed methods can be determined using diagnostic methods known in the art, e.g., by assaying plasma glucose and/or insulin levels. For instance, suitable subjects can include humans having a fasting blood glucose concentration (e.g., after a 8 to 10 hour fast) higher than about 100 mg/dL, higher than about 110 mg/dL, higher than about 120 mg/dL, higher than about 150 mg/dL, or higher than about 200 mg/dL. Suitable subjects can also include humans having a two hour postprandial blood glucose concentration of more than about 140 mg/dL, more than about 150 mg/dL, or more than about 200 mg/dL. Glucose concentration can also be presented in the units of millimole per liter (mmol/L), which can be acquired by dividing mg/dL by a factor of 18.

V. Methods of Preparing Microneedle Arrays

In some embodiments, the presently disclosed subject matter provides a method of preparing a microneedle array for the glucose-sensitive delivery of a diabetes treatment agent (e.g., insulin or a bioactive derivative thereof). In some embodiments, the method can comprise:

(a) preparing an aqueous solution of a vesicle and/or nanoparticle of the presently disclosed subject matter;
(b) dispersing said aqueous solution into a mold comprising a plurality of microneedle cavities, thereby providing a filled mold;
(c) drying the filled mold to remove water; and
(d) removing the mold to provide a microneedle array.

In some embodiments, the method can further comprise cross-linking polymeric materials in the microneedle array. For example, in some embodiments, a chemical cross-linker (e.g., N,N-methylenebisacrylamide) and/or photoinitiator can be added to the mold prior to drying. In some embodiments, the cross-linking can be performed by exposure to UV irradiation after the mold is removed.

In some embodiments, an additional polymer can be added to the mold prior to drying. The additional polymer can be the same or different from the hydrophilic polymer of the amphiphilic polymeric material. In some embodiments, the additional polymer is a modified hyaluronic acid, such as an alkylene-modified and/or an acrylate-modified hyaluronic acid.

In some embodiments, the filling of the mold in step (b) can be performed under vacuum and/or can involve centrifuging the mold (e.g., to aid in efficient and/or increased packing of the vesicles in the microneedle cavities).

In some embodiments, the mold can be dried in a dessicator or a vacuum desiccator.

In some embodiments, the mold can comprise a polymer, such as silicone (e.g., polydimethylsiloxane (PDMS)). The mold can comprise about 10, 50, 100, 250, 500, 1000 or more microcavities. The tip-to-tip spacing between tips of the microcavities can be between about 100 microns and about 1000 microns (e.g., about 100, 150, 200, 250, 300, 350, 400, 450, 500, 550, 600, 650, 700, 750, 800, 850, 900, 950, or about 1000 microns).

In some embodiments, the prepared microarray can be packaged, e.g., for storage or shipment. For example, the packaging can include polymer film, such as a moisture and/or gas impervious polymer film. The arrays can be packaged individually or in multi-array packs.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

In general, in vitro and in vivo results presented are Mean±the standard error of the mean. Statistical analysis was performed using Student's t-test or ANOVA test. With a p value <0.05, the differences between experimental groups and control groups were considered statistically significant.

Example 1

Representative Synthesis of Hypoxia-Sensitive Hyaluronic Acid

Hypoxia-sensitive hyaluronic acid (HS-HA) was synthesized by chemically conjugating HA with 6-(2-nitroimidazole)hexylamine though amide formation. All chemicals were purchased from Sigma-Aldrich (St. Louis, Mo., United States of America) unless otherwise specified and were used as received. Sodium hyaluronic acid (molecular weight 300 kiloDaltons (kDa) was purchased from Freda Biochem Co., Ltd. (Shandong, China).

First, 6-(2-nitroimidazole)hexylamine was synthesized for reaction with the carboxylic acids of HA. In brief, nitroimidazole (NI, 0.15 g, 1.3 mmol) was dissolved in DMF, to which $K_2CO_3$ (0.28 g, 2.0 mmol) was added. Then, 6-(tert-butyloxycarbonylamino)hexyl bromide (i.e., 6-(BOC-amino)hexylbromide, 0.39 g, 1.4 mmol) was added dropwise into the solution and stirred at 80° C. for 4 h. The solid impurities were removed from the reaction mixture by filter and washed with methanol. The residual solvent was then evaporated to obtain the solid product, which was suspended in deionized (DI) water and extracted with ethyl acetate. The organic layer was collected and dried over sodium sulfate, and then concentrated. The product was re-dissolved in methanol on ice. Five (5) mL of 1.25 M HCl in methanol was added to the solution and stirred for 24 h at room temperature (RT), after which the solvent was removed from the using a rotary evaporator to obtain the amine-functionalized NI. Next, 6-(2-nitroimidazole)hexylamine was conjugated to HA in the presence of N-(3-dimethylaminopropyl)-N'-ethylcarbodiimide hydrochloride (EDC) and N-hydroxysuccinimide (NHS). Briefly, 0.24 g of HA (molecular weight: ~300 kDa) was dissolved in water, to which EDC (0.56 g, 3.4 mmol) and NHS (0.39 g, 3.4 mmol) were added and stirred for 15 min at RT. Then 6-(2-nitroimidazole)hexylamine (0.18 g, 0.85 mmol) was added to the mixture at RT for 24 h. The reaction solution was thoroughly dialyzed against a 1:1 mixture of DI water and methanol for 1 day and against DI water for 2 days. Then, HS-HA was obtained by lyophilization and characterized by $^1H$ NMR (Varian GEMINI 2300; Varian Inc., Palo Alto, Calif., United States of America).

6-(2-nitroimidazole)hexylamine: $^1H$ NMR (DMSO-$d_6$, 300 MHz, δ ppm): 1.30-1.78 (m, 8H, $NH_2CH_2(CH_2)_4$), 2.73 (s, 2H, $NH_2CH_2$), 4.38 (s, 2H, $NCH_2$), 7.19 (s, 1H), 7.87 (s, 1H).

HS-HA: $^1H$ NMR ($D_2O$, 300 MHz, δ ppm): 1.88-2.40 (m, 8H, $NH_2CH_2(CH_2)_4$), 2.87-3.19 (m, 4H, $NH_2CH_2$, $NCH_2$), 7.19 (s, 1H), 7.48 (s, 1H).

Example 2

Synthesis and Characterization of Glucose-Responsive Vesicles (GRVs)

GRVs were prepared by self-assembly in aqueous solution. Briefly, 20 mg of amphiphilic HS-HA was dissolved in water/methanol (2/1, v/v), followed by addition of 10 mg human insulin and 1.0 mg GOx. Human recombinant insulin (Zinc (Zn) salt, 27.5 international units per milligram (IU/mg)) was purchased from Life Technology (Carlsbad, Calif., United States of America). The emulsion was stirred at 4° C. for 2 hours. Then the methanol was removed by dialysis against DI water for 1 day. The pH value of the resulting GRV solution was adjusted to 5.3 (the isoelectric point (pi) of insulin) in order to remove unloaded insulin by centrifugation at 8,000 rpm for 10 min and further filtered by a centrifugal filter (100,000 Da molecular mass cutoff, Millipore, Billerica, Mass., United States of America) at pH 7.4. The final GRV solution was stored at 4° C. for later study. The insulin loading capacity (LC) of the GRVs was determined by measuring the loaded insulin content using a Coomassie Plus protein assay (Thermo Fisher Scientific Inc., Waltham, Mass., United States of America). The zeta potential and size distribution of the GRVs were measured on a particle sizer sold under the tradename ZETASIZER™ (Nano ZS, Malvern Instruments Ltd., Malvern, United Kingdom). Transmission electron microscope (TEM) images of GRVs were obtained on a JEOL 2000FX TEM instrument (JEOL USA, Inc., Peabody, Mass., United States of America).

Thus, GRVs were formed by self-assembly of a hypoxia-sensitive hyaluronic acid, encapsulating recombinant human insulin and GOx in the core. See FIG. 1A. The HS-HA was obtained via the formation of an amide bond with amine-functionalized NI in three steps as described in Example 1. The incorporation of hydrophobic NI groups renders the derived HA amphiphilic, enabling the formation of GRVs in the aqueous solution. Moreover, NI provides a hypoxia-sensitive element, which is expected to be bio-reduced under hypoxic conditions. See Nunn et al., Eur. J. Nucl. Med, 22(3):265-280 (1995); and Takasawa et al., Stroke, 39(5): 1629-1637 (2008). The reduced product with amine groups is water-soluble, leading to disassembly of GRVs. See FIG. 1A.

Figure 2A:
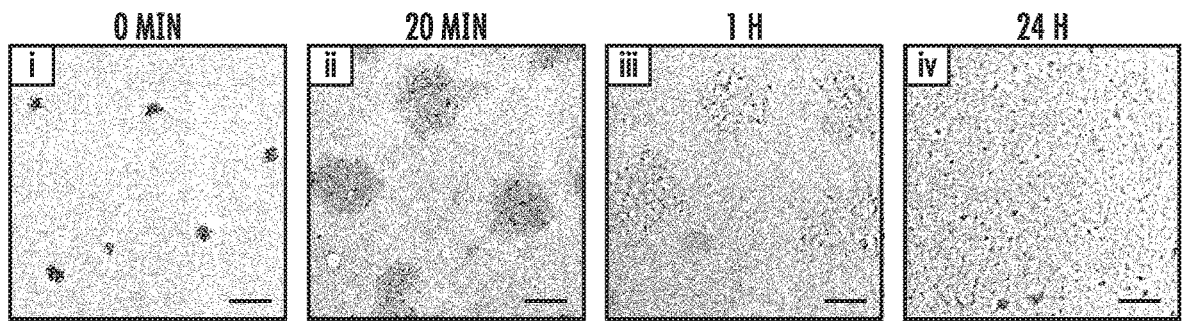
FIG. 2A is a series of transmission electron microscopy (TEM) images of glucose-responsive vesicles (GRVs) loaded with insulin and glucose oxidase (i) prior to incubation in a 400 milligram per deciliter (mg/dL) glucose solution, (ii) after twenty minutes of incubation in a 400 mg/dL glucose solution, (iii) after one hour of incubation in a 400 mg/dL glucose solution, or (iv) after 24 hours of incubation in a 400 mg/dL glucose solution.
Figure 2B:
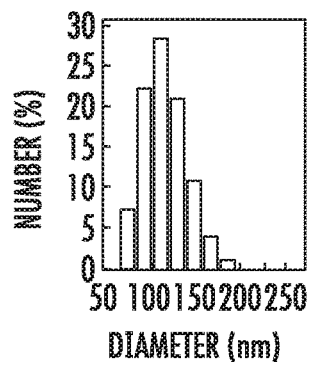
FIG. 2B is a bar graph showing the size distribution of glucose-responsive vesicles (GRVs) prior to incubation in a 400 milligram per deciliter (mg/dL) glucose solution.
Figure 2C:
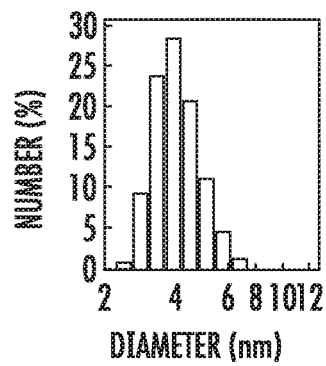
FIG. 2C is a bar graph showing the size distribution of glucose-responsive vesicles (GRVs) after incubation in a 400 milligram per deciliter (mg/dL) glucose solution for 24 hours.
Figure 2D:
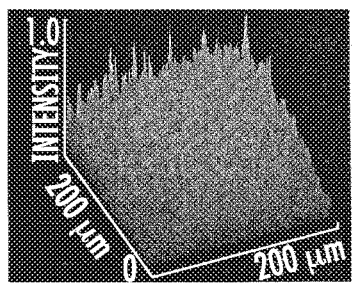
FIG. 2D is a 2.5 dimensional (2.5D) fluorescence image of a solution of fluorescein isothiocyanate (FITC)-insulin loaded glucose-responsive vesicles (GRVs) prior to incubation in a 400 milligram per deciliter (mg/dL) solution of glucose.

The GRVs had a spherical shape with a mono-dispersed size. See FIG. 2A, left-hand TEM image. The average diameter of GRVs was determined as 118 nm by the dynamic light scattering (DLS) (see FIG. 2B), which is consistent with observation by TEM. The zeta-potential of GRVs was measured as −34.7±0.4 mV due to the residual carboxyl of HA. The fluorescence image of GRVs with fluorescein isothiocyanate (FITC)-labeled insulin further verified successful encapsulation of insulin. See FIG. 2D. The insulin loading capacity of GRVs was determined as 8.7%. If not exposed to hypoxic conditions, the obtained GRVs were highly stable and no significant precipitation was observed at 4° C. for one month.

Example 3

In Vitro Glucose-Responsive Insulin Relase of GRVs

To evaluate the glucose responsive capability of the GRVs, GRVs were incubated in 600 μL PBS buffer (NaCl, 137 mM; KCl, 2.7 mM; $Na_2HPO_4$, 10 mM; $KH_2PO_4$, 2 mM; pH 7.4) with 100 μM NADPH and 5 μg/mL cytochrome c reductase. Various amounts of glucose were added to provide solutions with a final glucose concentration of 0 mg/dL, 100 mg/dL or 400 mg/dL. The 400 mg/dL glucose concentration solution represents a typical hyperglycemic glucose level, the 100 mg/dL glucose concentration solution represents a normglycemic glucose level, and the 0 mg/dL glucose concentration solution was used as a control. The mixtures were incubated at 37° C. in a container with an oxygen concentration of 21% by regulation with a mass-flow meter. At predetermined times, the pH value of each mixture was recorded using a pH meter (AB15, Thermo Fisher Scientific Inc., Waltham, Mass., United States of America), and then the pH value was adjusted to the pI of insulin to isolate the released insulin by centrifugation at 8,000 rpm for 10 min. The concentration of residual insulin encapsulated in the GRVs was examined using a Coomassie Plus protein assay (Thermo Fisher Scientific Inc., Waltham, Mass., United States of America). The absorbance was detected at 595 nm on an INFINITE® 200 PRO multimode plate reader (Tecan Group Ltd., Zurich, Switzerland), and the insulin content was calibrated with an insulin standard curve. For plotting the UV-Vis absorption of GRV solutions, the absorbance intensity was measured at 330 nm at set times. To assess the release profile of insulin from GRVs under different pH conditions, GRVs were incubated in PBS buffer at a pH 4.0 or at a pH of 7.4, both in the presence of 100 μM NADPH and 5 μg/mL cytochrome c reductase. The released insulin was measured using the same method mentioned above. The far-UV circular dichroism (CD) spectra of a native insulin solution and of a solution of insulin released from the GRVs (0.1 mg/mL) were analyzed using a CD spectrometer (Aviv Biomedical Inc., Lakewood, N.J., United States of America).

Figure 2E:
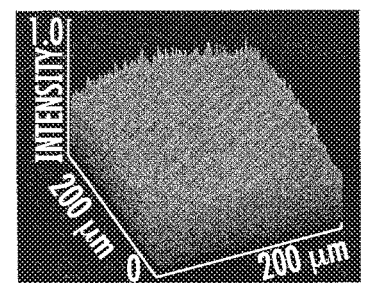
FIG. 2E is a 2.5 dimensional (2.5D) fluorescence image of a solution of fluorescein isothiocyanate (FITC)-insulin loaded glucose-responsive vesicles (GRVs) after incubation in a 400 milligram per deciliter (mg/dL) solution of glucose for 1 hour at 37 degrees Celsius (° C.).
Figure 2F:
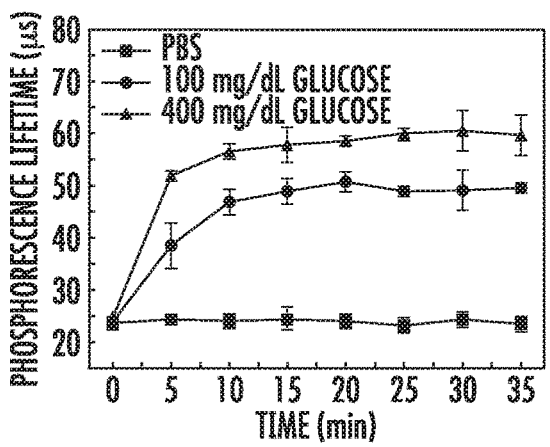
FIG. 2F is a graph showing the phosphorescence lifetime profile for glucose-responsive vesicles (GRVs) incubated with in glucose solutions containing different concentrations of glucose and containing an oxygen concentration molecule probe. Data is provided for GRVs incubated in a 100 milligram per deciliter (mg/dL) glucose solution (filled circles) and in a 400 mg/dL glucose solution (filled triangles). For comparison, data is provided for GRVs incubated in phosphate buffered saline (PBS) without glucose (filled squares).

Oxygen consumption, caused by the oxidation of glucose catalyzed by GOx, was measured using an oxygen-sensitive phosphorescent molecular probe. See Will et al., Nat. Protoc., 1(6):2563-2572 (2006); and Fercher et al., Acs Nano, 5(7):5499-5508 (2011). The sample exposed to the hyperglycemic solution had a lower oxygen concentration compared to the other two samples. See FIG. 2F. It rapidly achieved equilibrium in 10 minutes, suggesting that the oxygen consumption rate reached equilibrium with the dissolution rate. The recorded pH value of the solution of GRVs in a 400 mg/dL glucose solution decreased steadily over time, further substantiating the conversion of glucose to gluconic acid catalyzed by GOx.

Figure 2G:
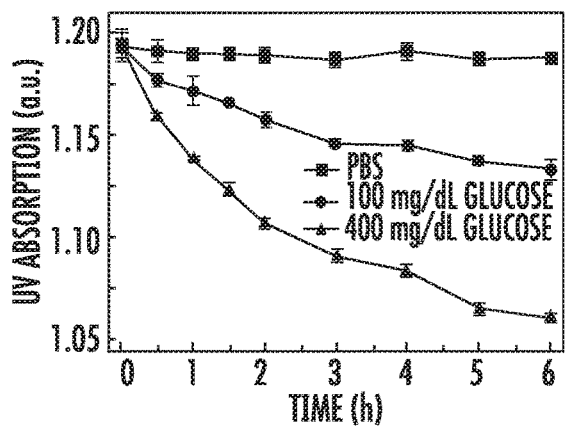
FIG. 2G is a graph showing the time dependent ultraviolet (UV) absorption (at 330 nanometers (nm)) of glucose-responsive vesicles (GRVs) in various glucose solutions at 37 degrees Celsius (° C.). Data is provided for GRVs incubated in a 100 milligram per deciliter (mg/dL) glucose solution (filled circles) and in a 400 mg/dL glucose solution (filled triangles). For comparison, data is provided for GRVs incubated in phosphate buffered saline (PBS) without glucose (filled squares). Error bars indicate standard deviation (s.d.) for three replicates.

In this hypoxic environment, the nitro groups of the HS-HA were effectively reduced by electrons from NADPH catalyzed by the reductase. According to the UV-Vis absorption spectra of the GRVs, the decrease of the characteristic peak of NI at 330 nm and the generation of a new peak at 280 nm, which corresponds to the characteristic peak of 2-aminoimidazole, also confirmed that the nitro group of NI was converted to the amine group via a reduction reaction under a hypoxic condition after a 2-hour incubation with a 400 mg/dL glucose solution. The residual concentration of NI was monitored in real time by measuring the UV-Vis absorbance at 330 nm. The corresponding intensity of GRVs incubated with the 400 mg/dL glucose solution gradually reduced over time (see FIG. 2G), suggesting the replacement of hydrophobic NI groups with amine groups in the core.

In contrast, a much slower decline of absorption intensity was observed in the samples associated with the 100 mg/dL glucose solution, and no decrease was observed in the control sample without glucose. Furthermore, corresponding evolutions of GRV conformation and size were observed through the TEM imaging and DLS. See FIG. 2A and FIG. 2C.

To further validate the release of insulin from the disassembled GRVs, insulin conjugated with FITC was encapsulated into GRVs. The fluorescence signal was more homogeneously distributed in the whole solution after 1 h, while the original GRV solution showed a large amount of cluster signal, suggesting the release of FITC-insulin over time. See FIG. 2E.

Figure 3A:
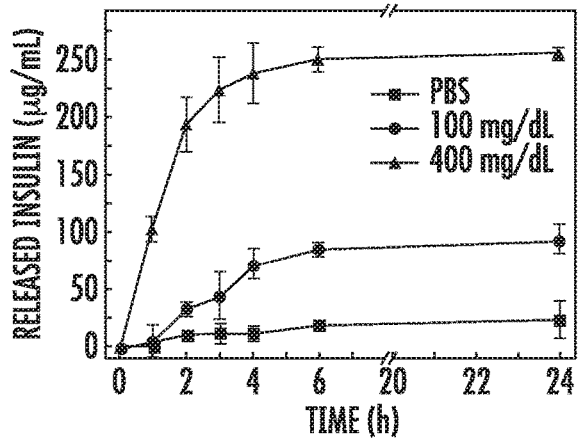
FIG. 3A is a graph showing the in vitro accumulated insulin release from glucose-responsive vesicles (GRVs) incubated in different glucose solutions of various glucose concentration (0 milligram per deciliter (mg/dL) glucose (i.e., PBS, filled squares); 100 mg/dL glucose (filled circles); and 400 mg/dL glucose (filled triangles) at 37 degrees Celsius (° C.).
Figure 3B:
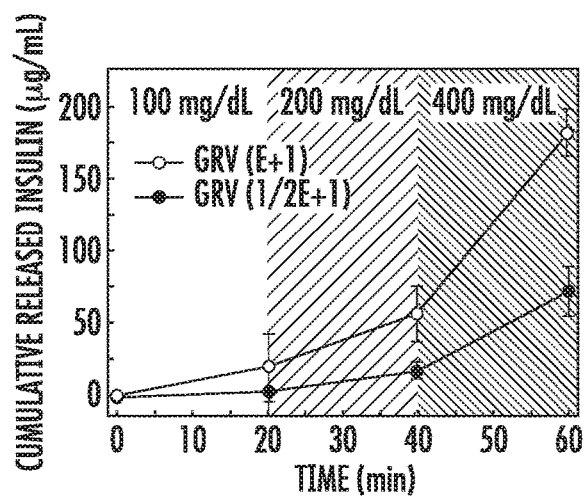
FIG. 3B is a graph showing self-regulated profiles of glucose-responsive vesicles (GRVs) containing glucose oxidase (GOx) and insulin (GRV (E+I), open circles) and similar GRVs containing half the amount of GOx (GRV(1/2E+I), filled circles). The rate of insulin release is shown as a function of glucose concentration (i.e., 100 milligrams per deciliter (mg/dL), 200 mg/dL, or 400 mg/dL).
Figure 3C:
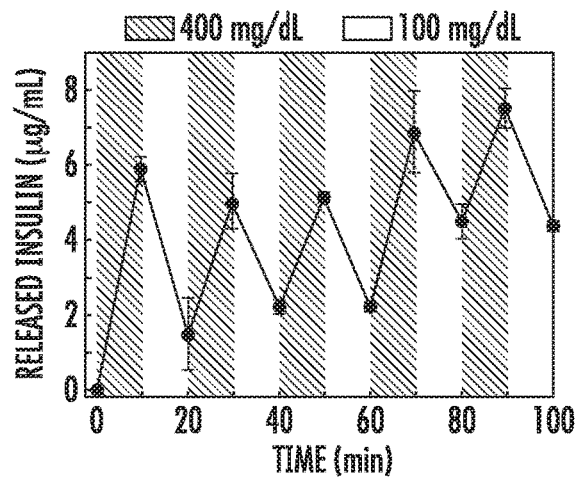
FIG. 3C is a pulsatile release profile of glucose-responsive vesicles (GRVs) exposed sequentially to a 100 milligram per deciliter (mg/dL) glucose solution for ten minutes and then a 400 mg/dL glucose solution for ten minutes for several repetitions.
Figure 3D:
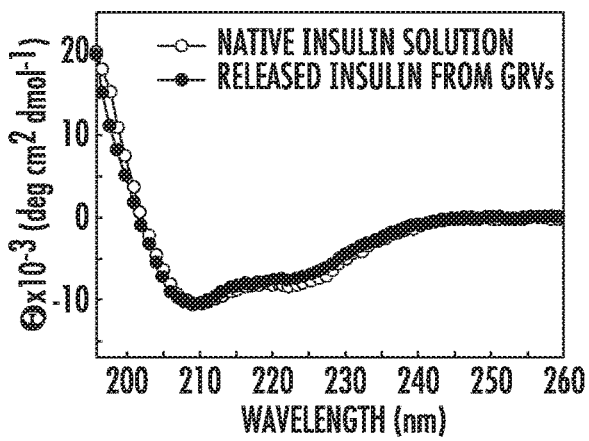
FIG. 3D is circular dichroism (CD) spectra of a native insulin solution (open circles) and of a solution of insulin released from glucose-responsive vesicles (GRVs) incubated in a 400 milligram per deciliter (mg/dL) glucose solution (filled circles). Error bars represent the standard deviation for three replicates.

A rapid insulin release profile was achieved from the GRVs incubated in the 400 mg/dL glucose solution due to the dissociation of GRVs, whereas only a small amount of insulin was released from the GRVs incubated in the PBS solutions with 0 or 100 mg/dL glucose. See FIG. 3A. In order to validate if the insulin release speed directly corresponds to the reduction of NI groups as a result of oxygen level rather than decreased pH level, the insulin release kinetic in pH=4.0 solution was investigated. The result showed that there was insignificant insulin release of the sample incubated in a pH=4.0 solution, confirming the GRVs are stable under an acidic condition. In addition, an alterable kinetic release profile of insulin was observed by varying glucose concentration. See FIG. 3B. A maximum 6.6 fold difference in insulin release rate was achieved when the glucose concentration was changed from 100 mg/dL to 400 mg/dL. In contrast, GRVs containing half the amount of GOx showed a slower release rate due to a relatively slower oxygen consumption rate, suggesting that the insulin release rate can be tuned by varying the encapsulation dose of enzyme. Moreover, the insulin release profile of GRVs presented a pulsatile pattern when alternatively exposed to normal and hyperglycemic state, changing states every 20 min for several cycles. See FIG. 3C. The GRVs responded to changes in glucose concentrations rapidly compared to existing synthetic closed-loop systems. See Mo et al., ChSRv, 43(10):3595-3629 (2014); and Veiseh et al., Nature Reviews Drug Discovery, 14(1):45-57 (2015). For example, the hypoxia-sensitive GRVs displayed a significantly faster response rate to hyperglycemic levels when compared to pH-sensitive triggered glucose-responsive nanoparticles previously reported (see Gu et al., ACS nano; 7(5):4194-4201 (2013)), with the same amount of enzymes. Without being bound to any one theory, it is believed that the faster response rate of the presently disclosed GRVs can be attributed to a faster achievement of a "structural transformation point" for dissociation of the formulation triggered by the local hypoxic microenvironment as opposed to triggering by local acidic environment. Collectively, the results suggest that the disassembly of the GRVs and the release of insulin is a glucose-mediated and hypoxia-dependent process. Additionally, the secondary conformational structure of the insulin released from the GRVs (0.1 mg/mL) was maintained to that of the native insulin, as indicated by the circular dichroism (CD) spectra. See FIG. 3D.

Example 4

Fabrication and Characterization of GRVs-Loaded Microneedle (MN)-Array Patch

To achieve convenient administration, a microneedle (MN)-array patch containing GRVs was prepared. The microneedle array patch can be both painless and disposable.

Figure 4B:
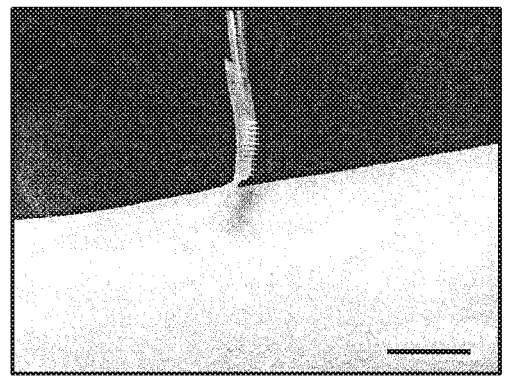
FIG. 4B is a photograph of an exemplary microneedle (MN) array of the presently disclosed subject matter. The scale bar on the bottom right of the photograph represents 1 centimeter (cm).
Figure 4C:
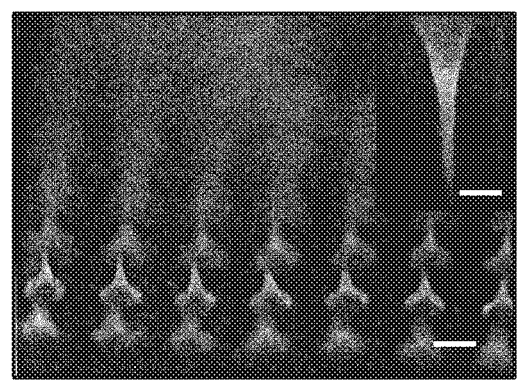
FIG. 4C is a fluorescence microscopy image of microneedles (MNs) loaded with glucose-responsive vesicles (GRVs) containing fluorescein isothiocyante (FITC)-labeled insulin. The inset is closer image of one of the microneedles. The scale bar represents 200 micrometers (μm).
Figure 4D:
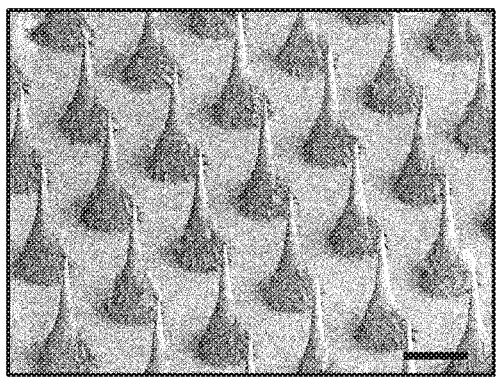
FIG. 4D is a scanning electron microscope (SEM) image of an exemplary microneedle (MN) array of the presently disclosed subject matter. The scale bar represents 200 micrometers (μm).
Figure 4E:
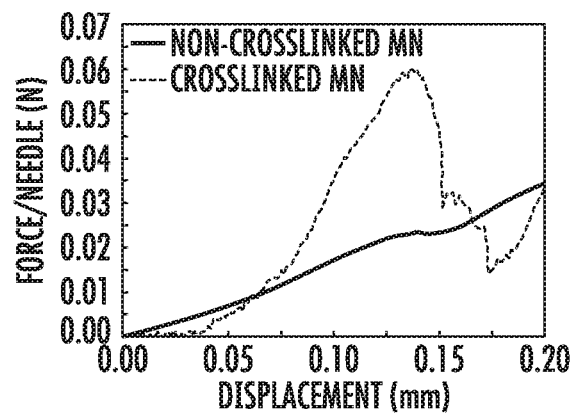
FIG. 4E is a graph showing the mechanical behavior of non-crosslinked and crosslinked glucose-responsive vesicle (GRV)-loaded miconeedles (MNs).

Briefly, the GRVs were first loaded in tips of a silicone mold for MNs by centrifugation, followed by dropwise addition of an acrylate-modified HA (m-HA) solution containing a crosslinker N,N'-methylenebisacrylamide (MBA) and photoinitiator. See FIG. 4A. Under UV irradiation, the HA-based needle matrix was photo-crosslinked, which can help to enhance the stiffness of the MNs and avoid undesired loss of GRVs from the needles. The obtained MNs had a conic shape and the needles were arranged in a 10×10 array with an area of 6×6 mm (see FIG. 4B), which was subsequently immobilized with medical tape. Each needle had a base radius of 150 µm, a height of 600 µm, and a tip radius of around 10 µm. See FIG. 4C. FIG. 4D shows the fluorescence image of a representative MN that contains FITC-insulin loaded GRVs, indicating that GRVs were evenly distributed inside. Furthermore, by measuring mechanical strength using a tensile compression machine, the failure force for crosslinked MN was determined as 0.06 N/needle, whereas the failure force was only 0.02 N/needle for non-crosslinked MN. See FIG. 4E. Accordingly, it appears that the stiffness of MNs improves with crosslinking, which can provide sufficient strength to facilitate skin insertion without breaking.

In order to investigate whether GRVs encapsulated in the MNs maintained glucose-responsive capability after MN fabrication, the tips of the needles containing GRVs were re-dissolved into PBS buffer, and treated with different glucose concentration solutions. There was negligible difference in release profile compared to the release profile of insulin from the original GRVs.

Example 5

In Vivo Studies of the Microneedles for Type 1 Diabetes Treatment

Figure 5A:
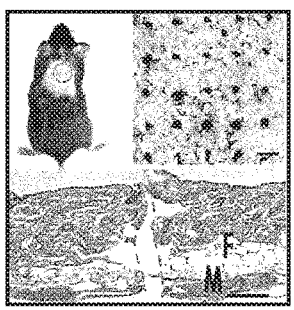
FIG. 5A is a group of images of: (top left) mouse dorsum and relevant skin (the area within the circle) transcutaneously treated with a microneedle (MN)-array patch of the presently disclosed subject matter; (top right) trypan blue staining showing MN penetration of the mouse skin; and (bottom) hematoxylin and eosin (H&E) stained section of mouse skin penetrated by one of the MNs. In the image on the top right, the scale bar represents 500 microns (μm). In the image on the bottom, the scale bar represents 100 microns (μm); muscle and fat tissues are indicated by "M" and "F", respectively; and the region where MN insertion took place is indicated by the dashed line.

To assess the in vivo efficacy of MN-array patches for diabetes treatment, streptozotocin (STZ)-induced type 1 diabetic mice (male C57B6, Jackson Lab, Bar Harbour, Me., United States of America) were grouped (five mice per group) and transcutaneously administered different patch samples on the dorsum (see FIG. 5A, top left), including: a blank MN patch containing only m-HA; a MN patch loaded with human recombinant insulin; a MN patch loaded with GRVs containing both insulin and enzyme (GRV(E+I)); a MN patch loaded with GRVs containing insulin and a half dose of enzyme (GRV(1/2E+I)); and a MN patch loaded with GRVs containing insulin only (GRV(I)). The insulin dose applied for each mouse was 10 mg/kg. The plasma-equivalent glucose was measured from tail vein samples (about 3 microliters) using the Clarity GL2Plus glucose meter (Clarity Diagnostics, Boca Raton, Fla., United States of America). Mouse glucose levels were monitored for two days before administration, and all mice were fasted overnight before administration of the different patches. The glucose levels of each mouse were monitored (at 5, 15, 30, 60 minutes and once per hour afterwards) until return to stable hyperglycemia.

In order to measure the plasma insulin concentration in vivo, 25 microliter blood samples were drawn from the tail vein of the mice at indicated time points. The serum was isolated and stored at −20° C. until assay. The plasma insulin concentration was measured using the Human Insulin ELISA kit (Calbiotech, Spring Valley, Calif., United States of America) according to the manufacturer's protocol.

The presently disclosed MN-array patches can effectively penetrate the dorsum skin of the mouse, as evidenced by the trypan blue staining (see FIG. 5A, top right) and hematoxylin and eosin (H&E) staining. See FIG. 5A, bottom. The blood glucose of treated mice in each group was monitored over time. The blood glucose in mice treated with a GRV(E+I)-loaded MN patch quickly declined to nearly 200 mg/dL within 0.5 h, and maintained at a normoglycemic state (<200 mg/dL) for up to 4 h before gradually increasing. See FIG. 5B. Without being bound to any one theory, this fast response rate appears attributable to the fast generation of a local hypoxic microenvironment that quickly activates the dissociation of GRVs; while the relatively low diffusion rate of oxygen in vivo compared to hydrogen ions can further facilitate this process. When the enzyme dose in the MNs for each mouse was reduced (from 1 mg/kg to 0.5 mg/kg), the blood glucose of mice treated with a GRV(1/2E+I)-loaded MN patch decreased to around 350 mg/dL within 0.5 h, and steadily increased afterward. In the absence of the enzyme, the glucose of mice administrated a GRV(I)-loaded MN patch did not show a noticeable decline, suggesting that the GRVs were stable in vivo. Correspondingly, mice administrated a GRV(E+I)-loaded MN patch presented a consistently higher plasma insulin concentration for at least 24 hours compared to those administrated GRV(1/2E+I)- or GRV(I)-loaded MN patches, as quantified by enzyme-linked immunosorbent assay (ELISA). See FIG. 5C. The SEM image of a GRV(E+I)-loaded MN patch inserted into skin showed collapsed tips after treatment (see FIG. 5D), further indicating that loaded GRVs disassemble and dissolve into subcutaneous tissues.

A glucose tolerance test was conducted to confirm the in vivo glucose responsiveness to MNs one hour post administration of a GRV(E+I)-loaded MN patch and a insulin-loaded MN patch. Briefly, mice were fasted overnight and administered a GRV(E+I)-loaded MN patch or a insulin-loaded MN patch, each with an insulin dose of 10 mg/kg for each mouse, and then a glucose solution in PBS was intraperitoneally injected into all mice at a dose of 1.5 g/kg. The glucose levels were monitored at 5, 10, 15, 20, 30, 40, 50, 60, 80, 100, and 120 minutes after injection. The glucose tolerance test on healthy mice was used as control. Similarly, healthy mice utilized to assess hypoglycemia were administered an insulin-loaded MN patch, a GRV(I)-loaded MN patch or a GRV(E+I)-loaded MN patch, but were not subjected to a glucose challenge.

Figure 5F:
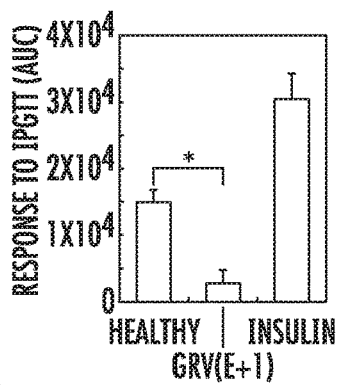
FIG. 5F is a graph showing responsiveness to intraperitoneally injected glucose in mice from the test described for FIG. 5E, calculated based on the area under the curve (AUC) in 120 minutes, with the baseline set at the zero-minute glucose reading.
Figure 5B:
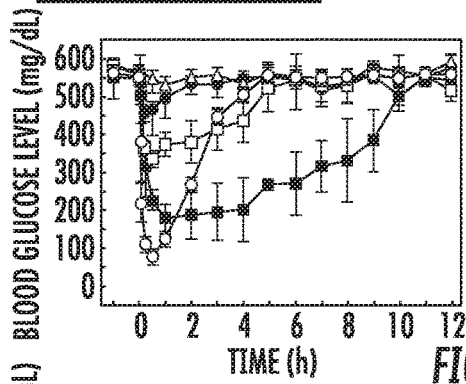
FIG. 5B is a graph of blood glucose levels during in vivo studies of glucose-responsive vesicle (GRV)-loaded microneedle (MN)-array patch treatment for type I diabetes in streptozotocin (STZ)-induced diabetic mice. Data is provided for mice treated with blank MN (MN not containing insulin or an enzyme, open triangles); MN loaded with GRVs containing human recombinant insulin only (GRV(I), filled circles); MN loaded with GRVs containing insulin and glucose oxidase enzyme (GRV(E+I), filled squares); and MN loaded with insulin and a half amount of enzyme (GRV(1/2E+I), open squares). As a control, data is provided for mice treated via insulin injection (open circles).
Figure 5G:
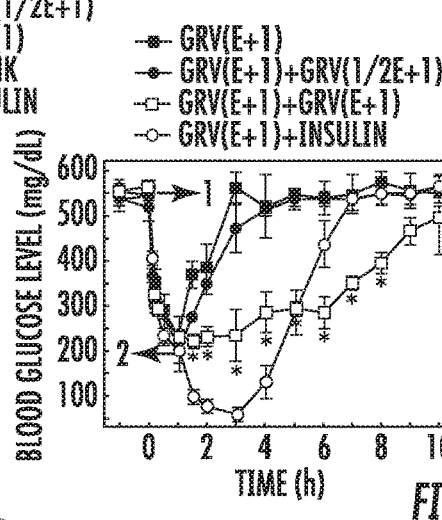
FIG. 5G is a graph showing blood glucose changes in mice treated with additional administration of a microneedle (MN) array patch one hour post administration of a first glucose-responsive vesicle (GRV)-loaded MN array patch, where the first GRV-loaded MN array patch contained GRVs loaded with insulin and glucose oxidase enzyme (i.e., GRV (E+I)). The additional MN array patch contained GRVs loaded with both insulin and glucose oxidase enzyme (GRV (E+I)+GRV(E+I), open squares); GRVs loaded with insulin and half the enzyme (GRV(E+I)+(GRV(1/2E+1), filled circles); or insulin only (GRV(E+I)+insulin, open circles). For comparison, data is also provided for mice that received no second MN array patch (GRV(E+I), filled squares). The black arrows indicate the administration time points of the first and second MN array patch.
Figure 5C:
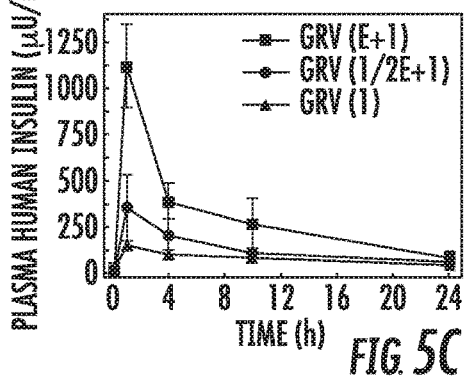
FIG. 5C is a graph of plasma insulin concentrations during in viva studies of glucose-responsive vesicle-loaded microneedle (MN)-array patch treatment for type I diabetes in streptozotocin (STZ)-induced diabetic mice. Data is provided for mice treated with a MN array loaded with human recombinant insulin only (GRV(I), filled triangles); a MN array loaded with insulin and glucose oxidase enzyme (GRV(E+I), filled squares); and a NM array loaded with insulin and half the amount of enzyme (GRV(1/2E+I), filled circles).
Figure 5H:
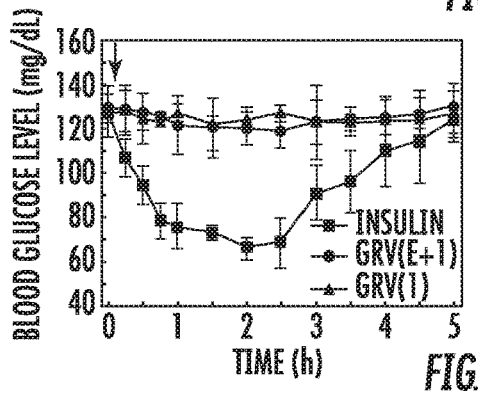
FIG. 5H is a graph of blood glucose changes in healthy mice treated with glucose-responsive vesicle (GRV)-loaded microneedle (MN) array patches over time. Data is provided for mice treated with a GRV-loaded MN array patch where the GRVs contained both insulin and glucose oxidase enzyme (GRV(E+I), filled circles) and where the GRVs contained only insulin (GRV(I), filled triangles). For comparison, data is provided for mice injected with insulin (Insulin, filled squares). The black arrow indicates the administration time point.
Figure 5D:
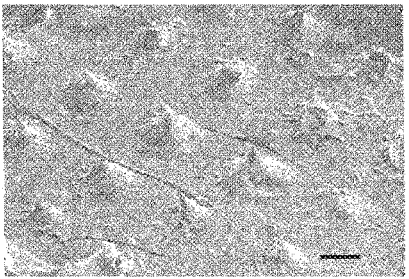
FIG. 5D is a scanning electron microscope (SEM) image of a glucose-responsive vesicle (GRV)-loaded microneedle (MN) array patch after insertion in mouse dorsum for 4 hours. The MNs were loaded with GRVs containing insulin and glucose oxidase enzyme (i.e., GRV(E+I)). The scale bar represents 200 microns (μm).
Figure 5E:
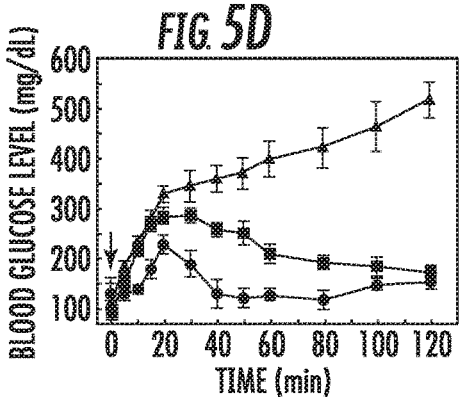
FIG. 5E is a graph of data obtained in an in vivo blood glucose tolerance test in diabetic mice one hour post administration of a glucose-responsive vesicle (GRV)-loaded microneedle (MN) array patch where the GRVs contained insulin and glucose oxidase enzyme (i.e., GRV(E+I), filled circles). For comparison, data is also shown for healthy mice (filled squares) and for diabetic mice one hour post administration of an MN array patch where the MNs are loaded only with insulin (filled triangles).

In the glucose tolerance test conducted at 1 h post-administration of MN patches, the control healthy mice exhibited a quick increase in blood glucose upon an intraperitoneal glucose injection, followed by a gradual decrease to normoglycemia. See FIG. 5E. The diabetic mice treated with a GRV(E+I)-loaded MN patch showed a delayed increase in blood glucose after glucose injection, and then a rapid decline to a normal state within 30 min. However, the glucose of the mice administrated an insulin-loaded MN patch did not decline in 120 min. The area under the curve was calculated between 0 and 120 min to measure MN responsiveness. As shown in FIG. 5F, the GRV(E+I)-loaded MN patch had a significantly fast response toward the glucose challenge.

Figure 5I:
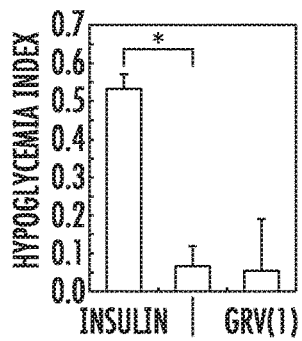
FIG. 5I is a graph of the quantification of the hypoglycemic index of the mice described for FIG. 5H. The hypoglycemic index was calculated from the difference between the initial and nadir blood glucose readings divided by the time at which nadir was reached. *P<0.05 for administration with a glucose responsive vesicle (GRV) microneedle (MN) array patch containing with GRVs loaded with enzyme and insulin (GRV(E+I)) compared with an insulin-loaded MN array patch (GRV(I)). Error bars indicate s.d. (n=5).

In order to further assess the in vivo glucose control capability of MNs, serial administration of MN patches was performed. The glucose level of mice treated with a first GRV(E+I)-loaded MN patch (insulin dose for each mouse: 5 mg/kg) quickly decreased to around 200 mg/dL within 1 h. See FIG. 5G. However, glucose did not further decrease to a hypoglycemic level upon application of another (i.e., a second) GRV(E+I)-loaded MN patch (insulin dose for each mouse: 5 mg/kg), and maintained glucose concentrations around 200 mg/dL for another 3 h. In contrast, the mice administered a second GRV(I)-loaded MN patch (insulin dose for each mouse: 5 mg/kg) or that did not receive an additional patch showed a rapid increase in glucose to a hyperglycemic state in 3 h. Another group of mice were subsequently administered an insulin-loaded MN patch and their blood glucose continued to decrease, leading to a potential risk of hypoglycemia. The study on the healthy mice further indicated there is little insulin leak in GRV-loaded MN patches, and they had reduced hypoglycemia risk compared with the insulin-loaded MN. See FIG. 5H. The corresponding hypoglycemia index (defined as the fall in glucose from initial reading to the nadir divided by the time over which this fall was reached) was calculated to quantitatively measure the extent to which insulin elicited hypoglycemia. GRV-loaded MNs showed a reduced hypoglycemic index compared to insulin-loaded MN when administrated in a normoglycemic state. See FIG. 5I. Moreover, HA is found throughout the human body and the bare GRVs did not show significant toxicity at various concentrations studied.

Example 6

Discussion of Examples 1-5

Current GOx-based glucose-responsive insulin delivery systems mainly utilize matrices consisting of pH-sensitive materials, which release insulin by either protonation or degradation due to enzymatic generation of gluconic acid. However, their effectiveness can be limited by slow response upon blood glucose changes, especially under a buffered physiological environment. The presently disclosed GRVs are believed to be the first demonstration of a glucose-responsive insulin delivery strategy based on a hypoxia-sensitive formulation instead of pH-sensitive ones. A local hypoxic microenvironment was rapidly generated in PBS buffer solution due to the enzymatic consumption of oxygen, as evidenced by an oxygen-sensitive phosphorescent probe. Subsequently, the hydrophobic side-chains of HS-HA were reduced into hydrophilic chains, resulting in disassembly of GRVs, subsequently increasing the release rate of insulin. A change in morphology of the GRVs was observed 20 min post incubation in PBS buffer with 400 mg/dL glucose by TEM, indicating the disassembly of GRVs. The in vitro insulin release profile of GRVs indicated a faster release rate than pH-sensitive based glucose-responsive nanoparticles previously reported. In addition, the insulin release kinetics could be adjusted by varying the enzyme dose both in vitro and in vivo, further implying that the release of insulin from the GRVs undergoes a glucose-mediated and hypoxia-dependent process.

The GRVs were integrated into a HA based MN-array patch for convenient, painless and continuous administration of insulin delivery. The crosslinked HA matrix not only helped to improve mechanical strength and skin penetration capability, but also appeared to restrict the loss of insulin from the GRVs to avoid burst release. Additionally, the framework of needle patches and vesicles were both made from HA, which is highly biocompatible.

The GRV(E+I)-loaded MNs exhibited excellent regulation of glucose in a normal range with faster responsiveness. Furthermore, besides the highly sensitive vesicles, the rapid uptake by the lymphatics through the transcutaneous administration can also contribute to the fast merits. The in vivo glucose tolerance test demonstrated GRV-loaded MNs were more responsive to glucose challenge, and could efficiently avoid a potential risk to hypoglycemia. In addition, the results of a serial administration with MNs showed that they could precisely control glucose in a normal range for more prolonged periods. Considering that the human insulin used in these Examples is relatively insensitive in mice, the real dose for potential human usage could be significantly lower. It is believed that the presently disclosed "smart insulin patch" offers a clinical opportunity for closed-loop delivery of insulin in a fast glucose-responsiveness, pain-free, and safe manner.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A microneedle array comprising a dried matrix comprising a diabetes treatment agent and a glucose-sensing moiety, wherein the dried matrix is designed to undergo a structural transformation in response to a glucose concentration change leading to glucose-stimulated release of the diabetes treatment agent, wherein the dried matrix comprises vesicles comprising an amphiphilic polymeric material comprising a hydrophilic polymer covalently conjugated to a hypoxia-sensitive hydrophobic group, wherein said hypoxia-sensitive hydrophobic group comprises a nitroimidazole that is capable of reduction in a hypoxic environment to form a hydrophilic moiety, and further wherein (i) the diabetes treatment agent and (ii) the glucose-sensing moiety are contained within the vesicle and wherein the glucose-sensing moiety is a glucose-oxidizing agent, wherein said microneedle array comprises a plurality of microneedles wherein each of said plurality of microneedles consists of the dried matrix and has a length of between about 20 and about 1000 microns, and wherein said microneedle array is provided as part of a skin patch.

2. The microneedle array of claim 1, wherein the hydrophilic polymer is biodegradable.

3. The microneedle array of claim 1, wherein the hydrophilic polymer is a polyamino acid, a synthetic block copolymer, or a polysaccharide.

4. The microneedle array of claim 3, wherein the hydrophilic polymer is a polyamino acid and wherein the polyamino acid is polyglutamic acid.

5. The microneedle array of claim 1, wherein said amphiphilic polymeric material comprises a hydrophilic polymer covalently conjugated to an amino group of an amino-substituted hydrophobic group precursor, thereby forming an amide between said amino group and a carboxylic acid group present on the hydrophilic polymer.

6. The microneedle array of claim 1, wherein the amphiphilic polymeric material comprises hyaluronic acid covalently conjugated to 6-(2-nitroimidazole)hexylamine.

7. The microneedle array of claim 1, wherein the glucose oxidizing agent is glucose oxidase (GOx).

8. The microneedle array of claim 1, wherein the diabetes treatment agent is an insulin or a bioactive derivative thereof, wherein the insulin or bioactive derivative thereof is selected from a human insulin, a recombinant human insulin, insulin from a non-human animal, a fast-acting insulin, a rapid-acting insulin analog, an intermediate-acting insulin, and/or a long-acting insulin.

9. The microneedle array of claim 1, wherein each of the microneedles has a tip having a radius of less than about 100 microns.

10. The microneedle array of claim 1, wherein each of the microneedles has a tip having a radius of about 10 microns and a base having a radius of about 150 microns.

11. The microneedle array of claim 1, wherein said patch comprises one or more backing layers and/or skin-compatible adhesives.

12. A closed-loop insulin delivery system comprising the microneedle array of claim 1 wherein the diabetes treatment agent is insulin.

13. A method of delivering a diabetes treatment agent, to a subject in need thereof, the method comprising: providing the microneedle array of claim 1; and applying said array to a skin surface of said subject, wherein when glucose comes into contact with the microneedle array, it is oxidized, thereby creating a hypoxic environment that results in the reduction of the nitroimidazole to form the hydrophilic moiety, leading to disruption of vesicles and release of a diabetes treatment agent contained in the vesicles.

14. The method of claim 13, wherein the release of the diabetes treatment agent is at a rate corresponding to the glucose concentration coming into contact with the microneedle array.

15. The method of claim 13, wherein the subject is diabetic.

16. The method of claim 13, wherein the diabetes treatment agent is an insulin or a bioactive derivative thereof.

17. A method of preparing a microneedle array for the glucose-sensitive delivery of a diabetes treatment agent, the method comprising:
   (a) preparing an aqueous solution of a vesicle comprising an amphiphilic polymeric material comprising a hydrophilic polymer covalently conjugated to a hypoxia-sensitive hydrophobic group, wherein said hypoxia-sensitive hydrophobic group comprises a nitroimidazole that is capable of reduction in a hypoxic environment to form a hydrophilic moiety, and further wherein (i) a diabetes treatment agent, and (ii) a glucose oxidizing agent are contained within said vesicle;
   (b) dispersing said aqueous solution into a mold comprising a plurality of microneedle cavities having a depth between about 20 and about 1000 microns, thereby providing a filled mold;
   (c) drying the filled mold to remove water; and
   (d) removing the mold to provide a microneedle array.

18. The method of claim 17, further comprising cross-linking polymeric materials in the microneedle array.

19. The method of claim 17, wherein prior to step (c), additional hydrophilic polymer and/or a chemical cross-linker are added to the mold.

20. The method of claim 19, wherein the mold is centrifuged after the addition of the additional hydrophilic polymer and/or chemical cross-linker.

21. The method of claim 19, wherein the additional hydrophilic polymer is a modified hyaluronic acid.

22. The method of claim 21, wherein the modified hyaluronic acid is an alkylene-modified and/or acrylate-modified hyaluronic acid.

23. The method of claim 17, wherein the diabetes treatment agent is an insulin or a bioactive derivative thereof.

* * * * *